(12) United States Patent
Yan et al.

(10) Patent No.: US 10,300,030 B2
(45) Date of Patent: May 28, 2019

(54) TRADITIONAL CHINESE MEDICINE COMPOSITION

(71) Applicant: Tasly Pharmaceutical Group Co., Ltd., Tianjin (CN)

(72) Inventors: Xijun Yan, Tianjin (CN); Naifeng Wu, Tianjin (CN); Shunnan Zhang, Tianjin (CN); Ping Li, Tianjin (CN); Zhengliang Ye, Tianjin (CN); Lihong Zhou, Tianjin (CN); Lianwen Qi, Tianjin (CN); Fenglian Zhang, Tianjin (CN); Minchao Qi, Tianjin (CN); Zhexuan Yang, Tianjin (CN); Wei Sun, Tianjin (CN); Jing Yu, Tianjin (CN); Hua Yang, Tianjin (CN); Peng Liu, Tianjin (CN); Xiaohui Ma, Tianjin (CN); Hai'ou Dong, Tianjin (CN); Wensheng Zhang, Tianjin (CN); Lanlan Zhang, Tianjin (CN); Chenming Li, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 14/910,088

(22) PCT Filed: Aug. 28, 2014

(86) PCT No.: PCT/CN2014/085362
§ 371 (c)(1),
(2) Date: Feb. 4, 2016

(87) PCT Pub. No.: WO2015/027929
PCT Pub. Date: Mar. 5, 2015

(65) Prior Publication Data
US 2016/0184249 A1 Jun. 30, 2016

(30) Foreign Application Priority Data

Aug. 29, 2013 (CN) .......................... 2013 1 0384234
Jan. 30, 2014 (CN) .......................... 2014 1 0044675

(51) Int. Cl.
| A61K 31/192 | (2006.01) |
| A61K 31/704 | (2006.01) |
| A61K 36/537 | (2006.01) |
| A61K 31/7028 | (2006.01) |
| A61K 31/11 | (2006.01) |
| A61K 31/216 | (2006.01) |
| A61K 31/343 | (2006.01) |
| A61K 31/352 | (2006.01) |
| A61K 36/258 | (2006.01) |

(52) U.S. Cl.
CPC ............ *A61K 31/192* (2013.01); *A61K 31/11* (2013.01); *A61K 31/216* (2013.01); *A61K 31/343* (2013.01); *A61K 31/352* (2013.01); *A61K 31/704* (2013.01); *A61K 31/7028* (2013.01); *A61K 36/258* (2013.01); *A61K 36/537* (2013.01)

(58) Field of Classification Search
None
See application file for complete search history.

(56) References Cited

FOREIGN PATENT DOCUMENTS

| CN | 1414011 | | 4/2003 |
| CN | 1650876 | | 8/2005 |
| CN | 1759855 | A | 4/2006 |
| CN | 1772041 | A | 5/2006 |
| CN | 1879697 | A | 12/2006 |
| CN | 1951892 | | 4/2007 |
| CN | 101508965 | | 8/2009 |
| CN | 102526186 | A | 7/2012 |
| CN | 102675407 | | 9/2012 |
| CN | 102757336 | | 10/2012 |
| CN | 102908355 | A | 2/2013 |
| EP | 1741439 | A1 | 1/2007 |
| EP | 2415749 | A1 | 2/2012 |

OTHER PUBLICATIONS

Vermerris, W., & Nicholson, R. (2007). Phenolic compound biochemistry. Springer Science & Business Media.*
Zhang, Y., Jiang, P., Ye, M., Kim, S. H., Jiang, C., & Lü, J. (2012). Tanshinones: sources, pharmacokinetics and anti-cancer activities. International journal of molecular sciences, 13(10), 13621-13666.*
Vincken, J. P., Heng, L., de Groot, A., & Gruppen, H. (2007). Saponins, classification and occurrence in the plant kingdom. Phytochemistry, 68(3), 275-297.*
Qiao, Z., Ma, J., & Liu, H. (2011). Evaluation of the antioxidant potential of Salvia miltiorrhiza ethanol extract in a rat model of ischemia-reperfusion injury. Molecules, 16(12), 10002-10012. (Year: 2011).*
Wei et al., "Analysis of chemical and metabolic components in traditional Chinese medicinal combined prescription containing Radix Salvia miltiorrhiza and Radix Panax notoginseng by LC-ESI-MS methods," Biomedical Chromatography, Biomed. Chromotogr. 21: 7970809 (2007), Apr. 12, 2007, Wiley InterScience, 13 pages.

* cited by examiner

Primary Examiner — Eric Olson
Assistant Examiner — Dale R Miller
(74) Attorney, Agent, or Firm — Nixon Peabody LLP

(57) ABSTRACT

A traditional Chinese medicine composition and preparation thereof for treating cardiovascular diseases is provided. The traditional Chinese medicine composition consists of: by weight percentage, phenolic acid derivatives 30%~80%, tanshinones 2%~10% and saponins 15%~60%.

20 Claims, 19 Drawing Sheets

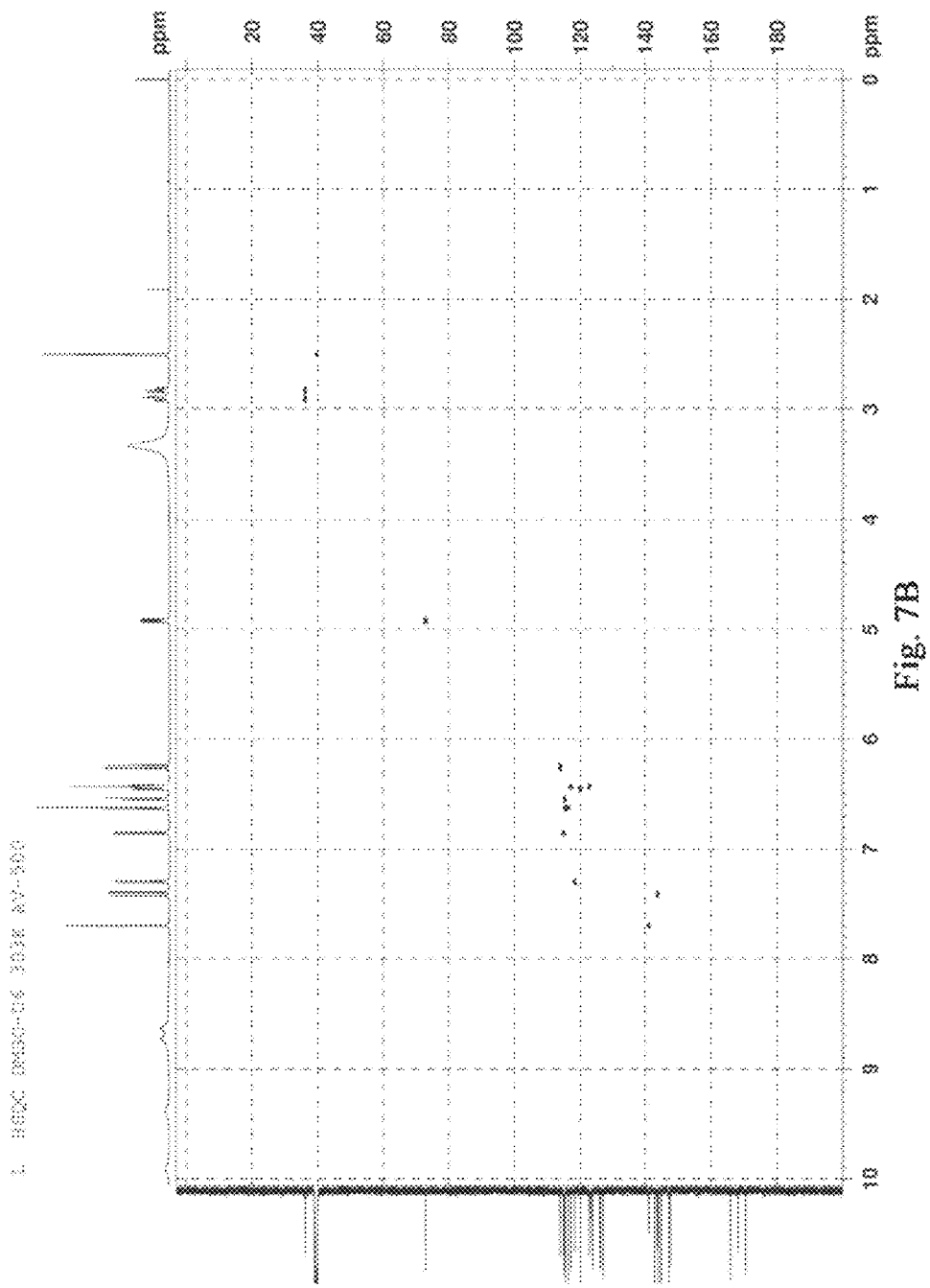

TRADITIONAL CHINESE MEDICINE COMPOSITION

CROSS-REFERENCE TO RELATED APPLICATIONS

This application is a U.S. national stage of PCT/CN2014/085362, filed on Aug. 28, 2014, which claims priority to Chinese Patent Application No. 201310384234.6, filed on Aug. 29, 2013 and Chinese Patent Application No. 201410044675.6, filed on Jan. 30, 2014, the contents of which are each incorporated herein by reference in its entirety.

FIELD OF THE INVENTION

Present invention relates to the field of medicine. More specifically, the invention relates to a traditional Chinese medicine composition for treating cardiovascular disease and a preparation thereof.

BACKGROUND OF THE INVENTION

With the improvement of living standards, worldwide population aging and younger onset population, the patients with cerebral and cardiovascular diseases are increased year by year. It has become the second large disease that does harm to human health. Angina pectoris is a clinical syndrome which is characterized in chest pain and chest discomfort, caused by myocardial temporary ischemia and hypoxia. Coronary heart disease (CHD) angina pectoris means the pectoris induced by myocardial ischemia and hypoxia that is caused by coronary arteriosclerosis or spasm, accounting for about 90% of the patients with angina pectoris.

Now, the methods for treating angina pectoris are dominated by dilating vessels, reducing blood viscosity and inhibiting platelets aggregation as well as anticoagulation. Traditionally, the chemicals include the nitrate, nitrite, β-receptor blocker and calcium antagonist. However, due to the stronger toxicity and side effect, these drugs are not suitable to use for long time. In addition, most of them focus on symptomatic treatment with no more effect on disease progress. Occasionally, symptoms occur after administrating the nitroglycerin, for example the head pain, head throbbing, speed-up heartbeat and even syncope (see *New Pharmaceutics*, 14$^{th}$ edition, p 264). Recently, the nitroglycerin was reported to have problems of inducing severe hypotension (see *China Journal of Morden Medicine*, 1997, 7 (4): 42, *Shanxi Medicine Journal*, 1996, 25(2) 315) and of being prone to producing tolorance (see Nanfang Journal of Nursing, 1996, 3(5):7~9). Hence, this hindered its application in clinic.

The phenolic acid derivatives of traditional Chinese medicine are widely distributed in the medicinal plants, e.g. Honeysuckle (*Lonicera japonica* Thunb.), Roots of *Rubus crataegifolius* (Rosaceae), composite Dandelion and breviscpini, Labiatae *Salvia officinalis, Canarium bengalense* (Burseraceae) and Umbelliferae *Angelica Sinensis* and *Rhizoma Ligustici Chuanxiong* etc. More and more attentions have been paid to the pharmacological activities that were found in the phenolic acid derivatives of these plants, for example scavenging free radicals, anti-inflammation, anti-virus, regulating immune, anticoagulation and anti-tumor etc. Usually, the phenolic acid derivatives are categorized as follows: the benzoic-acid-based phenolic acids, for example *Dioscorea bulbifera* L and Dandelion; the cinnamic-acid-based phenolic acids, for example, the ferulic acid, a cheif bio-active component in the water-soluble extract of *Angelica Sinensis* (Oliv.), *Rhizoma Ligustici Chuanxiong* and Dandelion; the lithospermic acid that is isolated from *Salviae Miltiorrhizae* Bge (Fam. Labiatae); the phenylacetic-acid-based phenolic acids, for example the p-hydroxyphenylacetic acid found in Dandelion and *Forsythia suspense*.

Tanshinone, also known as the total tanshinones, is the bacteriostatic fat-soluble phenanthraquinones extracted from the root of *Salviae Miltiorrhizae* Bge (Fam. Labiatae). More than 10 compounds have been identified, including the tanshinone I, tanshinone IIA, tanshinone IIB, cryptotanshinone and isocryptotanshinone etc. Wherein, 5 compounds of cryptotanshinone, dihydrotanshinone II, hydroxytanshinone, methyl tanshinate and tanshinone IIB are confirmed to have the antibacterial effect, as well as the effects of anti-inflammation and lowering temperature. Sodium tanshinone IIA sulfonate, a sulfonation product of tanshinone IIA, is water-soluble and clinically proven to have significant effect for treating angina pectoris and little side effect. It has been developed into a new drug for treating coronary heart disease (CHD). Multple effects have been found in the total tanshinones in anti-bacterium, diminishing inflammation, activating blood by removing stasis and promoting wound repair, and there is no significant side effect after long term of administration.

Saponine is a glucoside, which has triterpene or spirostane aglycones and is mainly distributed in land higher plants. The main components in lot of Chinese herbs, e.g. the Ginseng, Balloonflower and bupleurum include saponines. The saponines are confirmed to have the bioactivities of anticancer, inhibiting proliferation of tumor cell, inducing apotosis, affecting cancer cell signal transduction and inhibiting tumor angiogenesis and tumor cell metastasis as well. Also, the saponines have the effects of reducing blood sugar and blood lipid, anti-virus and regulating immune, becoming a very popular research subject at home and abroad.

Radix *Salviae Miltiorrhizae*, bitter in flavor, slightly cold in property, comes from the root of *Salvia militiorrhiza* Bunge. It converges to heart and liver channel, having the functions of stopping pain by removing stasis, promoting blood circulation by activating blood and tranquilizing the mind by relieving restlessness etc. As shown in modern pharmacological study, Radix *Salviae Miltiorrhizae* has the effects of dilating coronary artery, ameliorating microcirculation, protecting heart, inhibiting and removing platelet aggregation, enhancing the resistance of organism to anoxia, and anti-hepatitis, anti-tumor and anti-virus. In 2001, it was reported by Institute of Pharmacology of Chinese Medical Academy that the water-soluble bioactive components totally amounted to 13 phenolic acids, which was found in Radix *Salviae Miltiorrhizae* and same generic plants, including salvianolic acid A, B, C, D, E, F, G, H, I, J, lithospermic acid, rosmarinic acid and isosalvianolic acid C (see *Bulletin of Medical Research*, 2001, 30(7)) and their pharmacological effects. In 2002, salvianolic acid K was identified structurally (see *Journal of Xinjiang Medical University*, 2002, 25(3)). The water-soluble bioactive components in Radix *Salviae Miltiorrhizae* were also studied abroad. In 1999, the study was carried out by US Georgetown University on bioactivity of 13 salvianolic acids in anti HIV integrase and other viruses and applied for US patent. It was indicated that Radix *Salviae Miltiorrhizae* was a very potential medicinal plant with commercially developing value.

CONTENT OF THE INVENTION

The objective of present invention is to provide a traditional Chinese medicine composition for treating acute myocardial infarction and acute myocardial ischemia. Said composition is composed of following materials by weight percentage: 30%~80% of phenolic acid derivatives, 2%~10% of tanshinones and 15%~60% of saponines.

Wherein, the phenolic acid derivatives are composed of following ingredients by weight parts:

Danshensu:protocatechuic acid:protocatechuic aldehyde: caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(2~6):(0.01~0.05):(1~3):(0.01~0.06): (0.5~2):(0.2~1):(0.05~0.3):(0.5~2):(0.2~1):(0.1~0.5): (0.1~0.5):(0.2~1).

Said tanshinones are composed of following ingredients by weight parts:

Dihydrotanshinone I:tanshinone I:cryptotanshinone:tanshinone IIA:Danshenxinkun D=(0.01~0.05):(0.05~0.1): (0.02~0.1):(0.1~0.5):(0.1~0.5).

Said saponines are composed of following ingredients by weight parts:

*Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.1~0.5):(1~4):(1~4):(0.2~0.7): (0.2~0.7).

In an embodiment of this invention, said composition may be prepared into various kinds of preparations, for example the injection, tablet, capsule, drop pill and micro drop pill etc.

In particular, the present invention comprises technical solutions, as follows:

1. A traditional Chinese medicine composition composed of following materials by weight percentage: 30%~80% of phenolic acid derivatives, 2%~10% of tanshinones and 15%~60% of saponines.

2. The composition according to $1^{st}$ paragraph, wherein said composition is composed of following materials by weight percentage: 50%~70% of phenolic acid derivatives, 2%~6% of tanshinones and 25%~45% of saponines.

3. The composition according to $1^{st}$ paragraph, wherein said composition is composed of following materials by weight percentage: 66% of phenolic acid derivatives, 3% of tanshinones and 31% of saponines.

4. The composition according to one of $1^{st}$~$3^{rd}$ paragraphs, wherein said phenolic acid derivatives are composed of following ingredients by weight parts:

Danshensu:protocatechuic acid:protocatechuic aldehyde: caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(2~6):(0.01~0.05):(1~3):(0.01~0.06): (0.5~2):(0.2~1):(0.05~0.3):(0.5~2):(0.2~1):(0.1~0.5): (0.1~0.5):(0.2~1).

5. The composition according to $4^{th}$ paragraph, wherein said phenolic acid derivatives are composed of following ingredients by weight parts:

Danshensu:protocatechuic acid:protocatechuic aldehyde: caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54): (0.03~0.04):(0.86~1.13):(0.48~0.63):(0.12~0.16):(1~2): (0.44~0.58):(0.27~0.36):(0.29~0.38):(0.54~0.64).

6. The composition according to one of $1^{st}$~$3^{rd}$ paragraphs, wherein said phenolic acid derivatives are composed of following ingredients by weight parts:

Danshensu:protocatechuic aldehyde:Salvianolic acid U+ Salvianolic acid T:Salvianolic D:Salvianolic acid G:rosmarinic acid:lithospermic acid:Salvianolic acid B:Salvianolic acid A=(3~5):(1~2):(0.5~2):(0.3~0.8):(0.1~0.5): (0.3~1.5):(0.1~0.3):(0.5~2):(0.5~1.5).

7. The composition according to $6^{th}$ paragraph, wherein said phenolic acid derivatives are composed of following ingredients by weight parts:

Danshensu:protocatechuic aldehyde:Salvianolic acid U+ Salvianolic acid T:Salvianolic D:Salvianolic acid G:rosmarinic acid:lithospermic acid:Salvianolic acid B:Salvianolic acid A=3.52:1.38:1.1:0.58:0.33:0.79:0.17:1.32:0.93.

8. The composition according to one of $1^{st}$~$7^{th}$ paragraphs, wherein said tanshinones are composed of following ingredients by weight parts:

Dihydrotanshinone I:tanshinone I:cryptotanshinone:tanshinone IIA:Danshenxinkun D=(0.01~0.05):(0.05~0.1): (0.02~0.1):(0.1~0.5):(0.1~0.5).

9. The composition according to $8^{th}$ paragraph, wherein said tanshinones comprise following ingredients by weight parts:

Dihydrotanshinone I:tanshinone I:cryptotanshinone:tanshinone IIA:Danshenxinkun D=(0.02~0.03):(0.06~0.07): (0.04~0.06):(0.21~0.27):(0.22~0.28).

10. The composition according to one of $1^{st}$~$7^{th}$ paragraphs, wherein said tanshinones are composed of following ingredients by weight parts:

Dihydrotanshinone I:tanshinone I:cryptotanshinone:tanshinone IIA=(0.01~0.05):(0.05~0.1):(0.02~0.1):(0.1~0.5).

11. The composition according to $10^{th}$ paragraph, wherein said tanshinones are composed of following ingredients by weight parts:

Dihydrotanshinone I:tanshinone I:cryptotanshinone:tanshinone IIA=0.03:0.08:0.03:0.26.

12. The composition according to one of $1^{st}$~$11^{th}$ paragraphs, wherein said saponines are composed of following ingredients by weight parts:

*Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.1~0.5):(1~4):(1~4):(0.2~0.7): (0.2~0.7).

13. The composition according to $12^{th}$ paragraph, wherein said saponines are composed of following ingredients by weight parts:

*Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.2~0.3):(1.9~3.0):(1.9~3.0): (0.48~0.51):(0.47~0.62).

14. The composition according to $13^{th}$ paragraph, wherein said Ginsenoside Rg1 and Ginsenoside Re coexist in a ratio of (16~17):1 by weight parts.

15. A preparation comprising the traditional Chinese medicine composition according to any one of $1^{st}$~$14^{th}$ paragraphs and a pharmaceutically acceptable carrier; preferably, the weight percentage of said composition in the preparation is 0.1%~99.9% and the balanced is the pharmaceutically acceptable carrier.

EMBODIMENTS

Figure 1A:
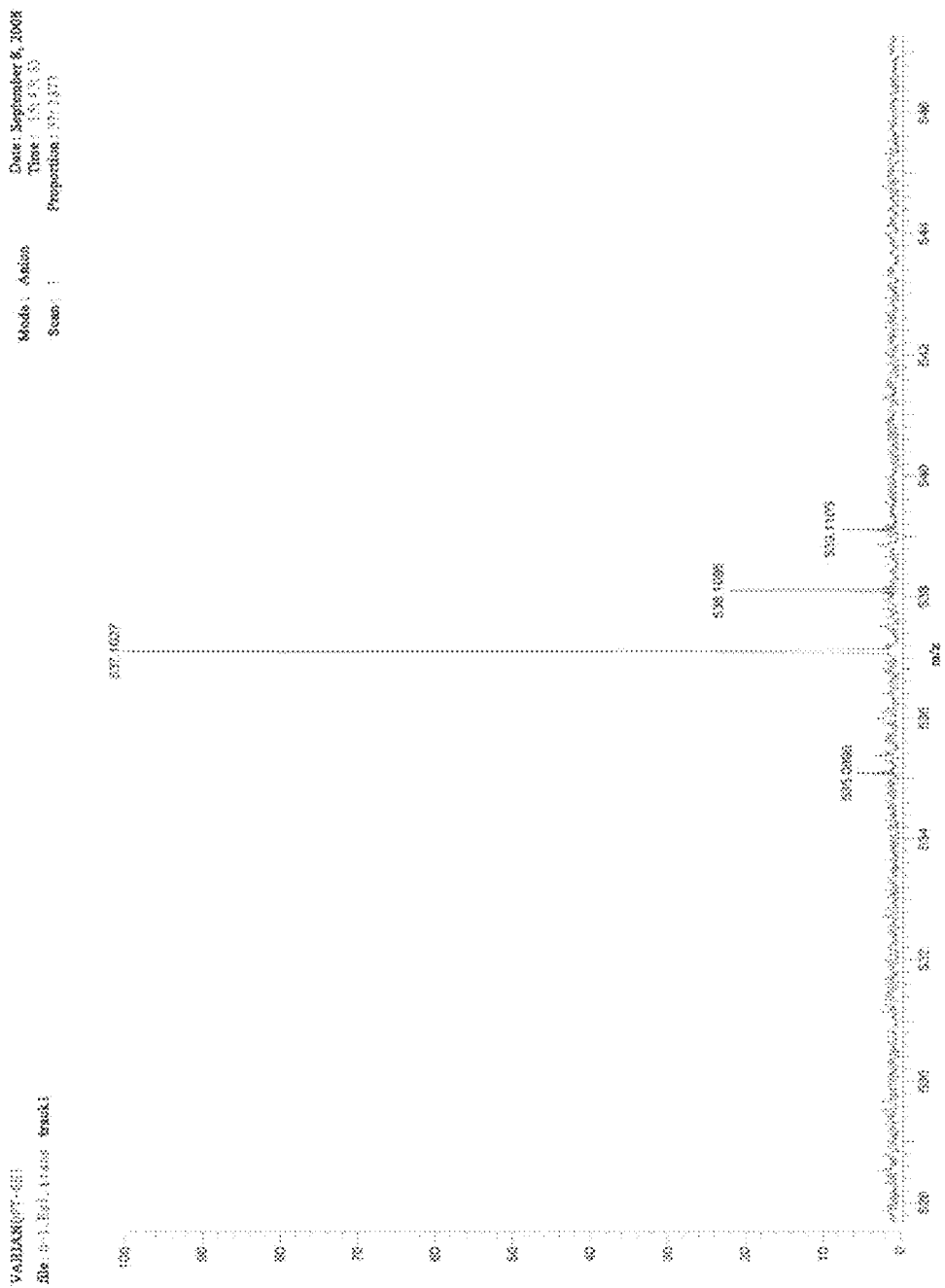
FIG. 1 was the high resolution mass spectrometry of salvianolic acid T, A: (R)-salvianolic acid T; B: (S)-salvianolic acid T.
Figure 1B:
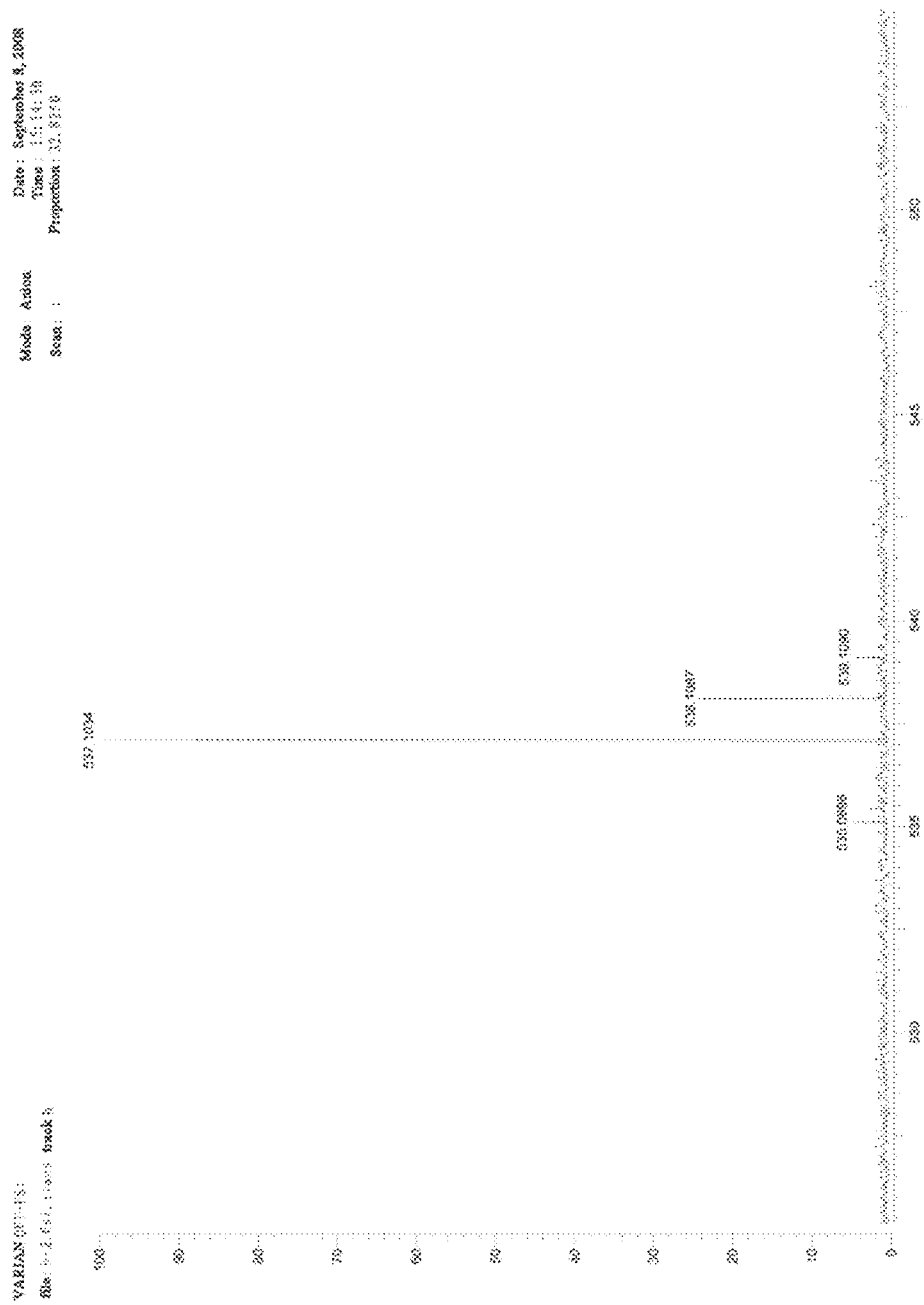
Figure 2A:
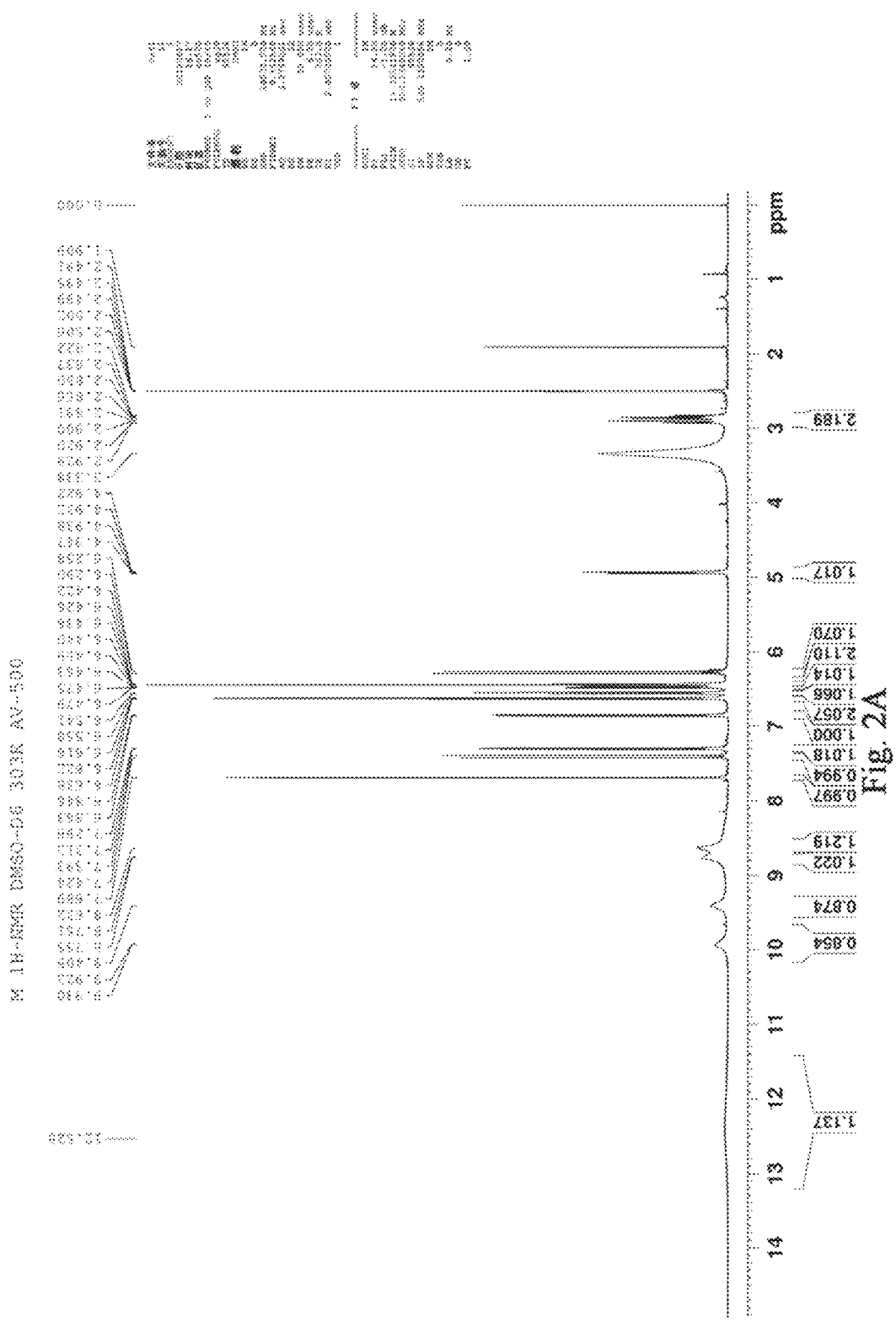
FIG. 2 was the $^{1}$H-NMR figure of salvianolic acid T (500 MHz, DMSO), A: (R)-salvianolic acid T; B: (S)-salvianolic acid T.
Figure 2B:
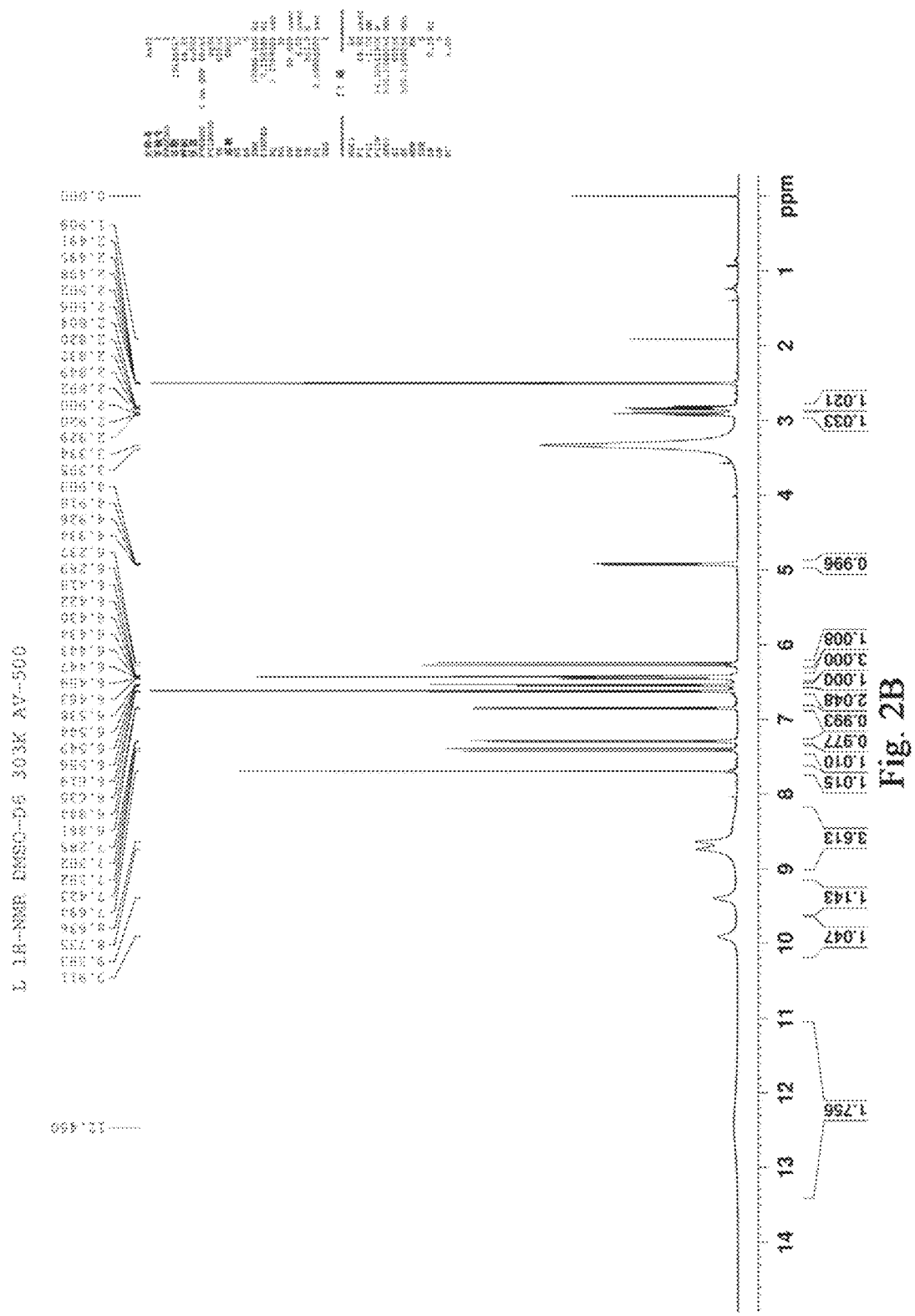
Figure 3A:
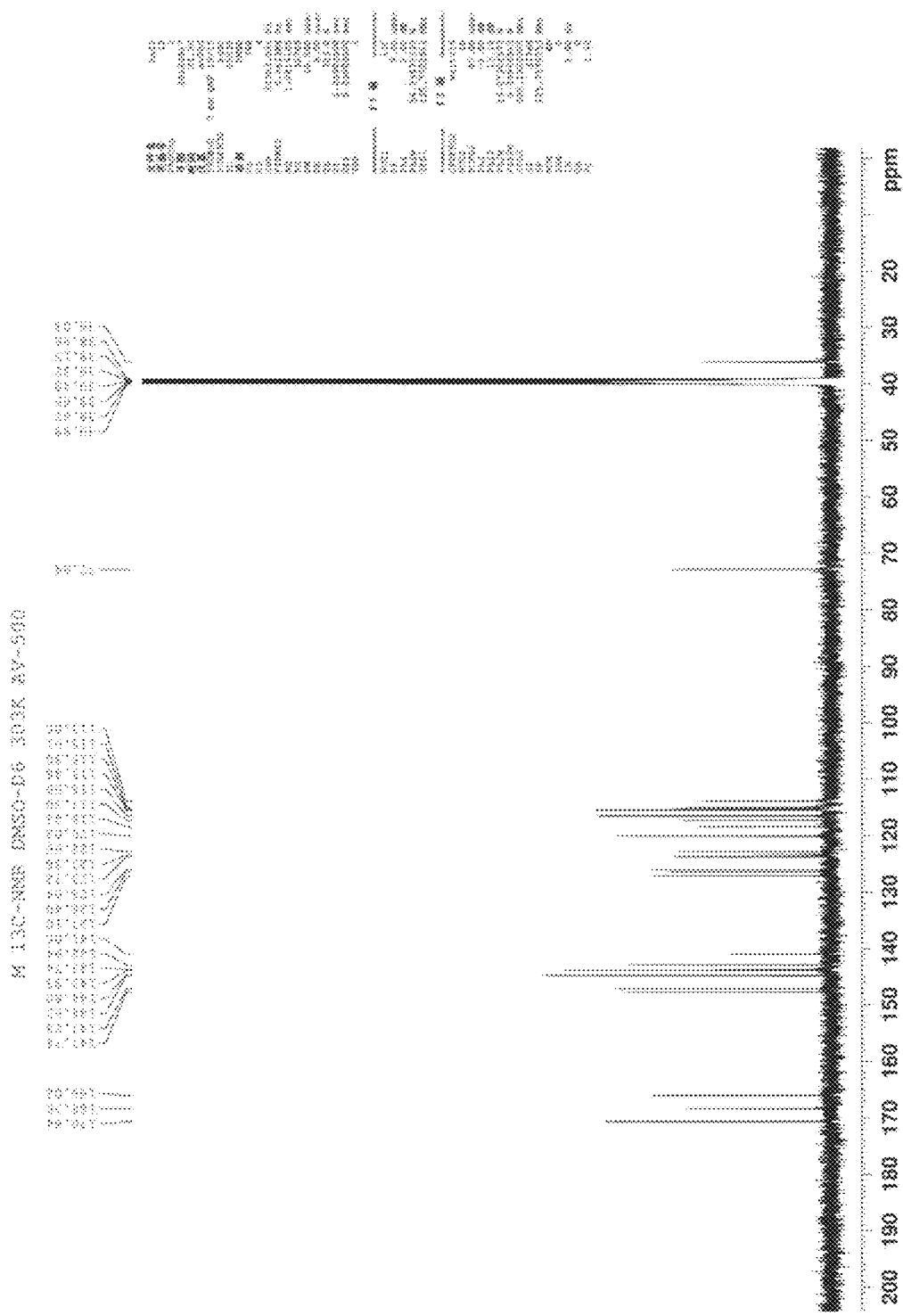
FIG. 3 was the $^{13}$C-NMR figure of salvianolic acid T (125 MHz, DMSO), A: (R)-salvianolic acid T; B: (S)-salvianolic acid T.
Figure 3B:
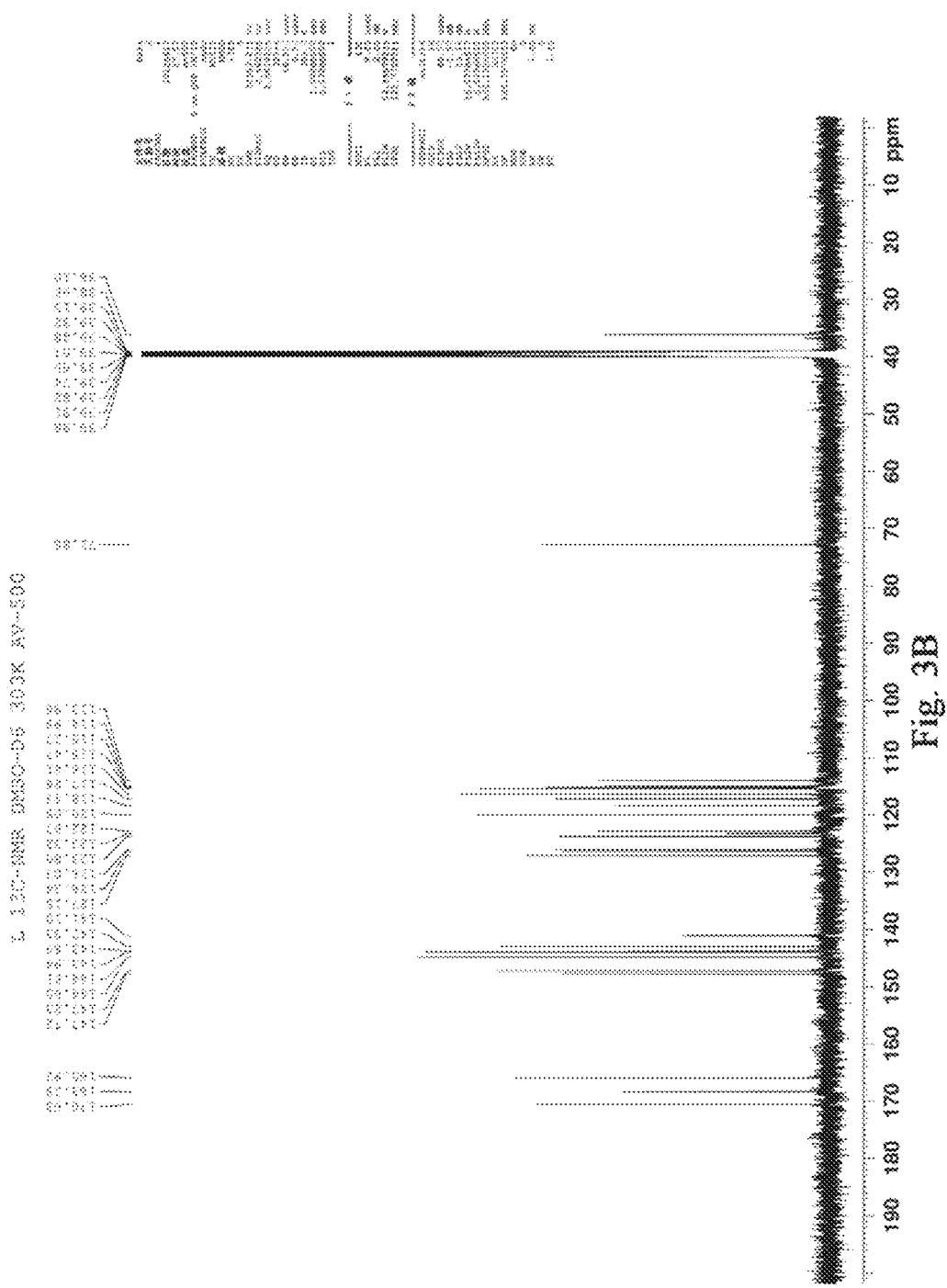
Figure 4A:
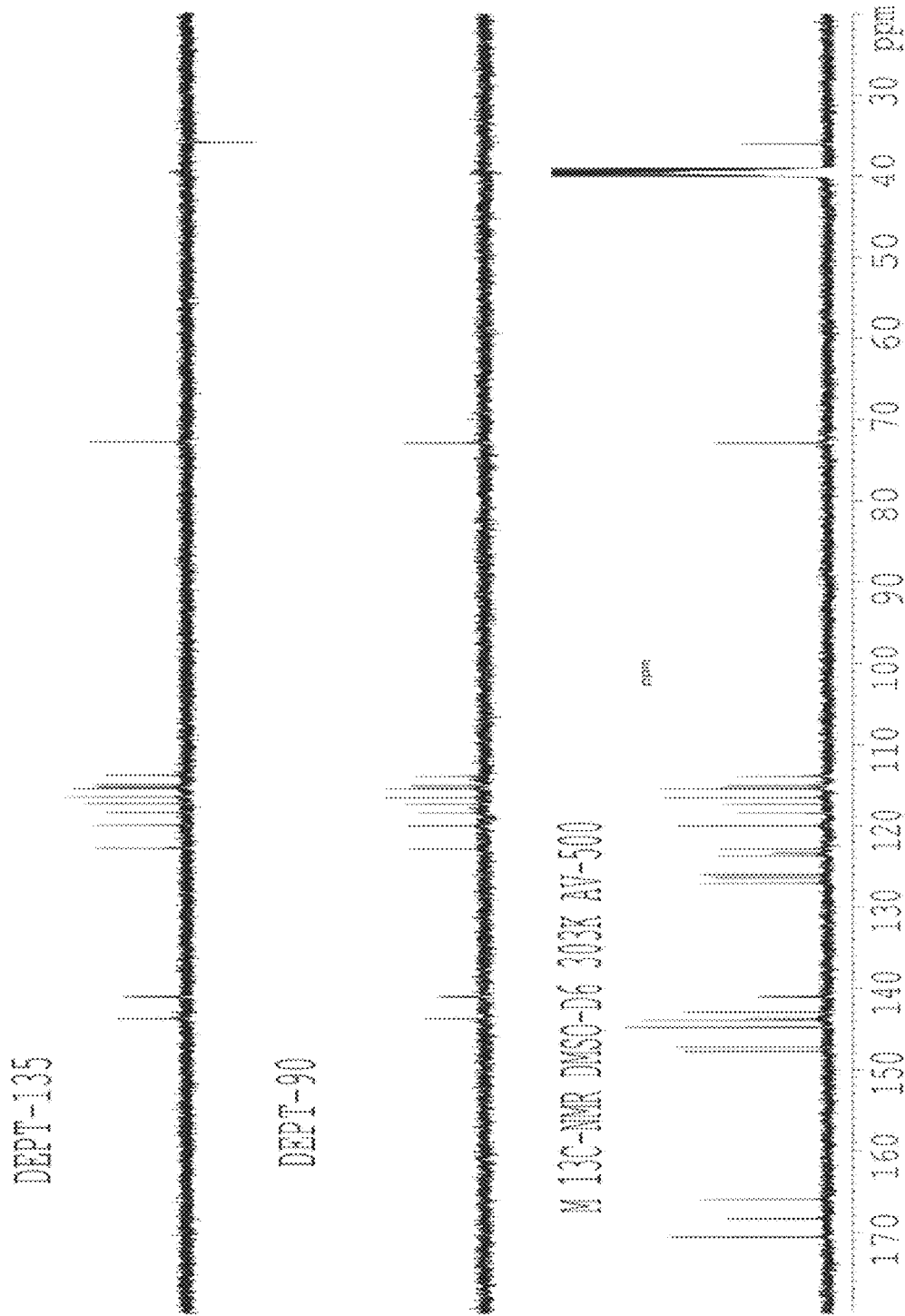
FIG. 4 was the DEPT figure of salvianolic acid T, A: (R)-salvianolic acid T; B: (S)-salvianolic acid T.
Figure 4B:
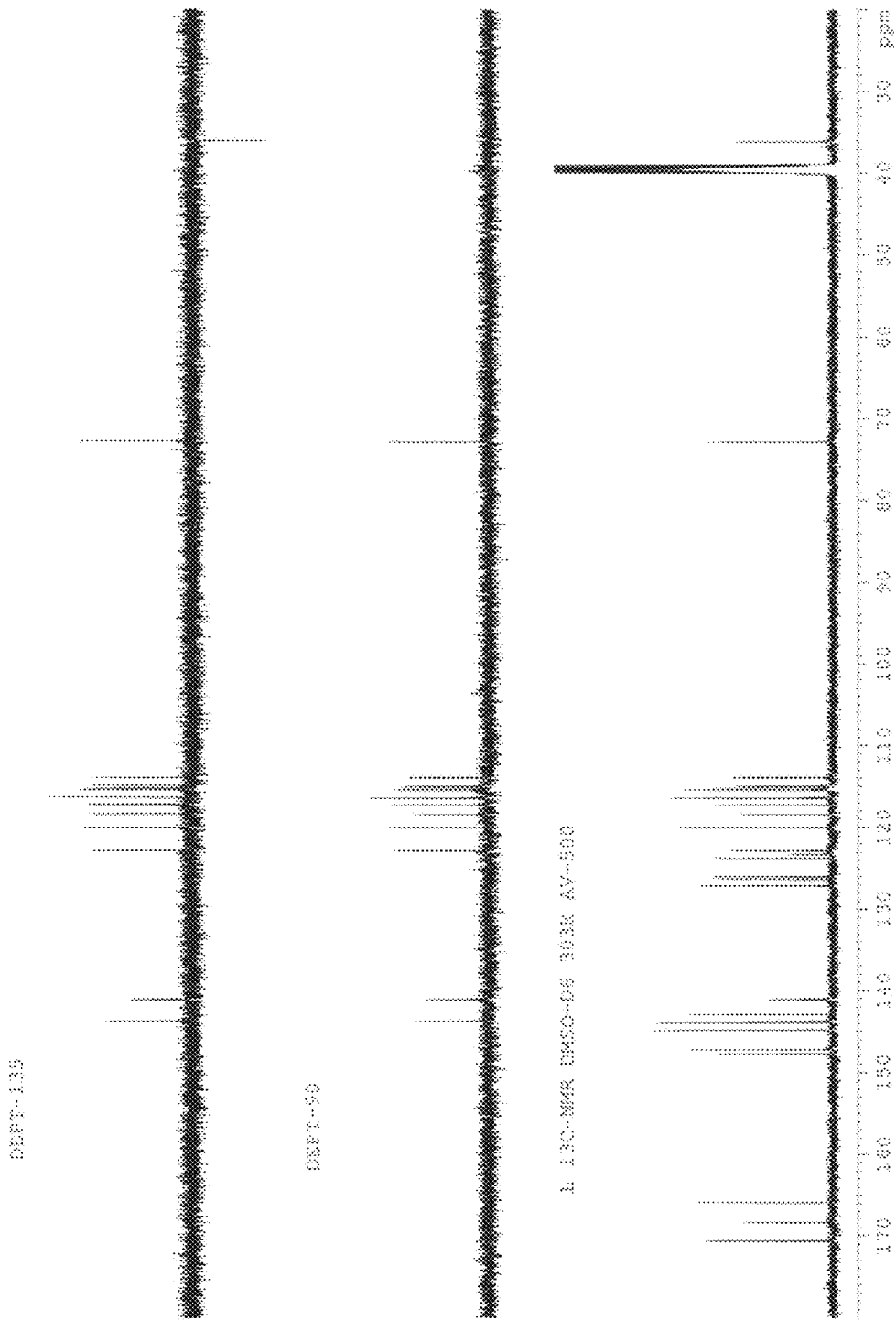
Figure 5A:
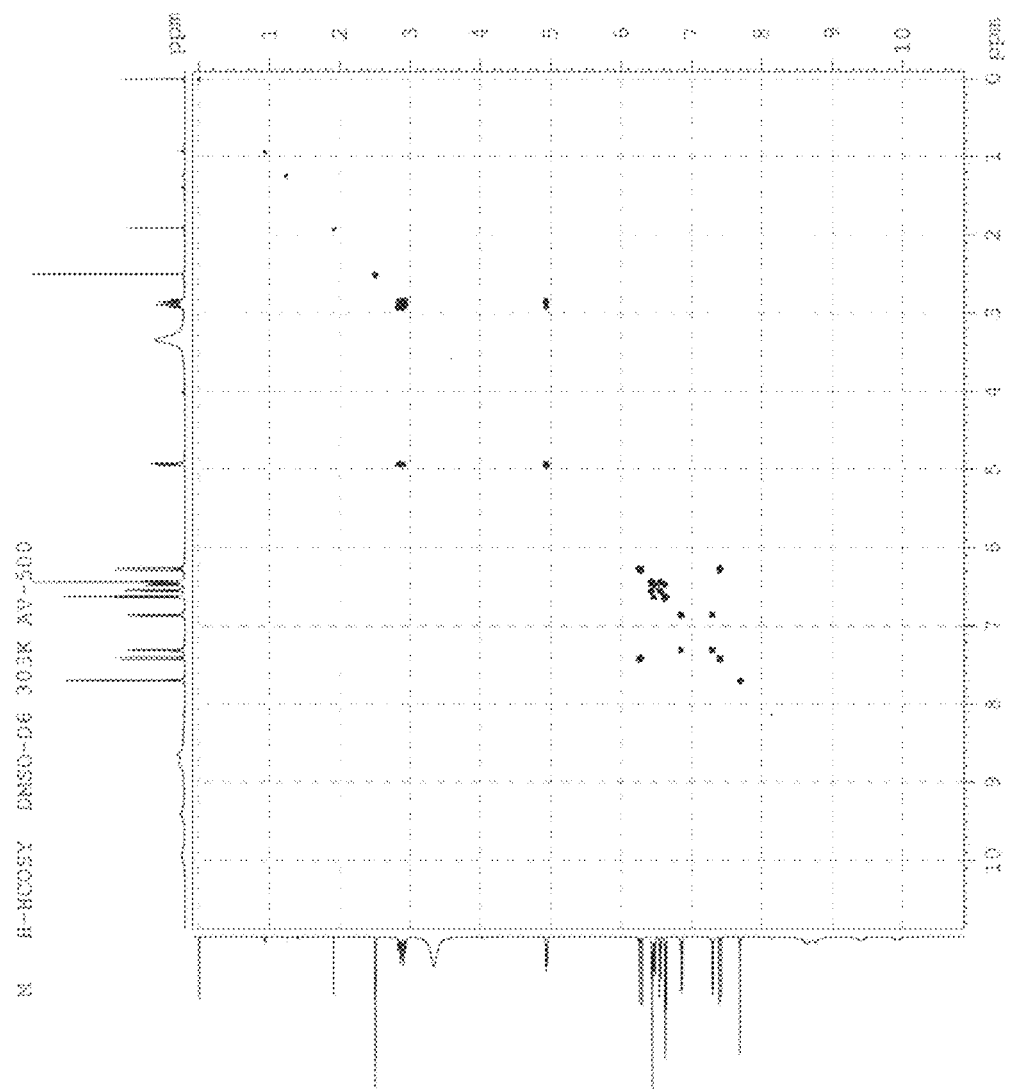
FIG. 5 was the COSY figure of salvianolic acid T, A: (R)-salvianolic acid T; B: (S)-salvianolic acid T.
Figure 5B:
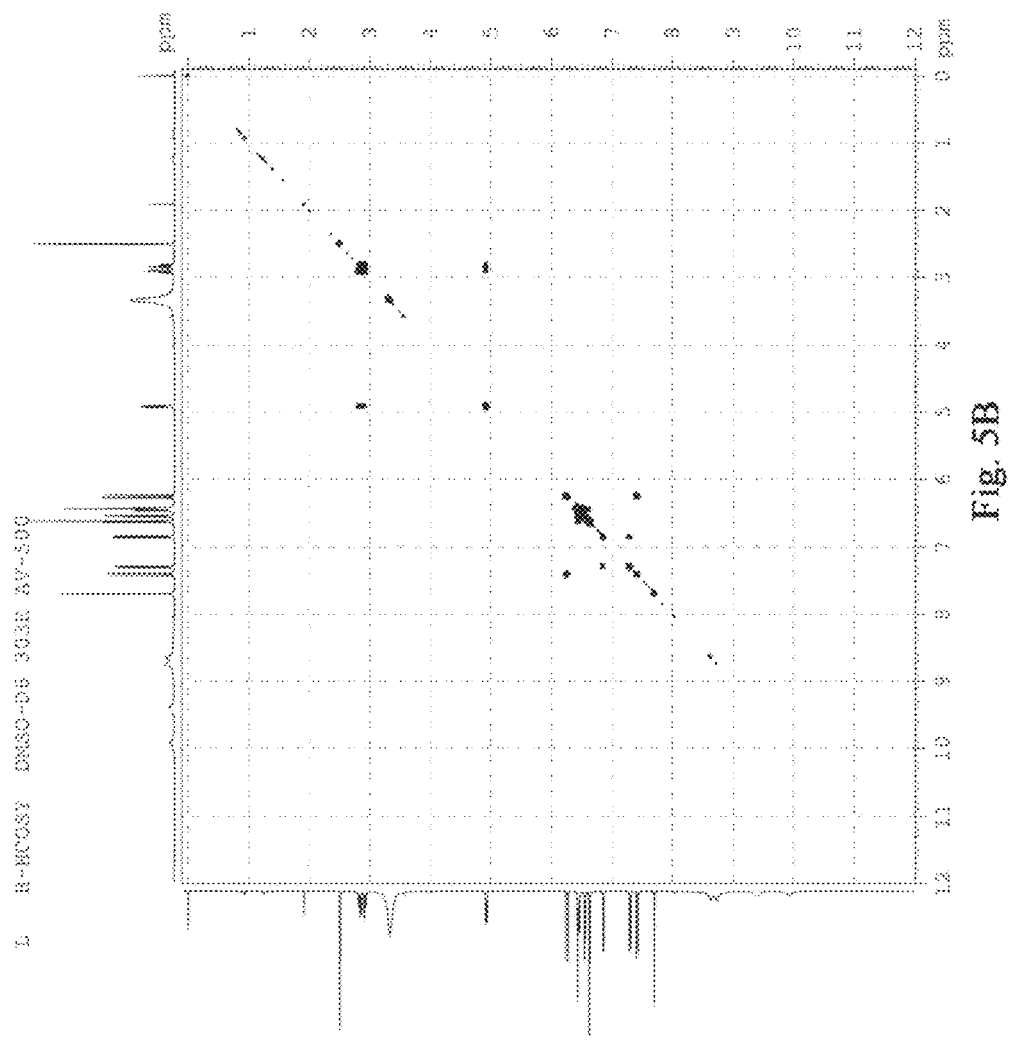
Figure 6A:
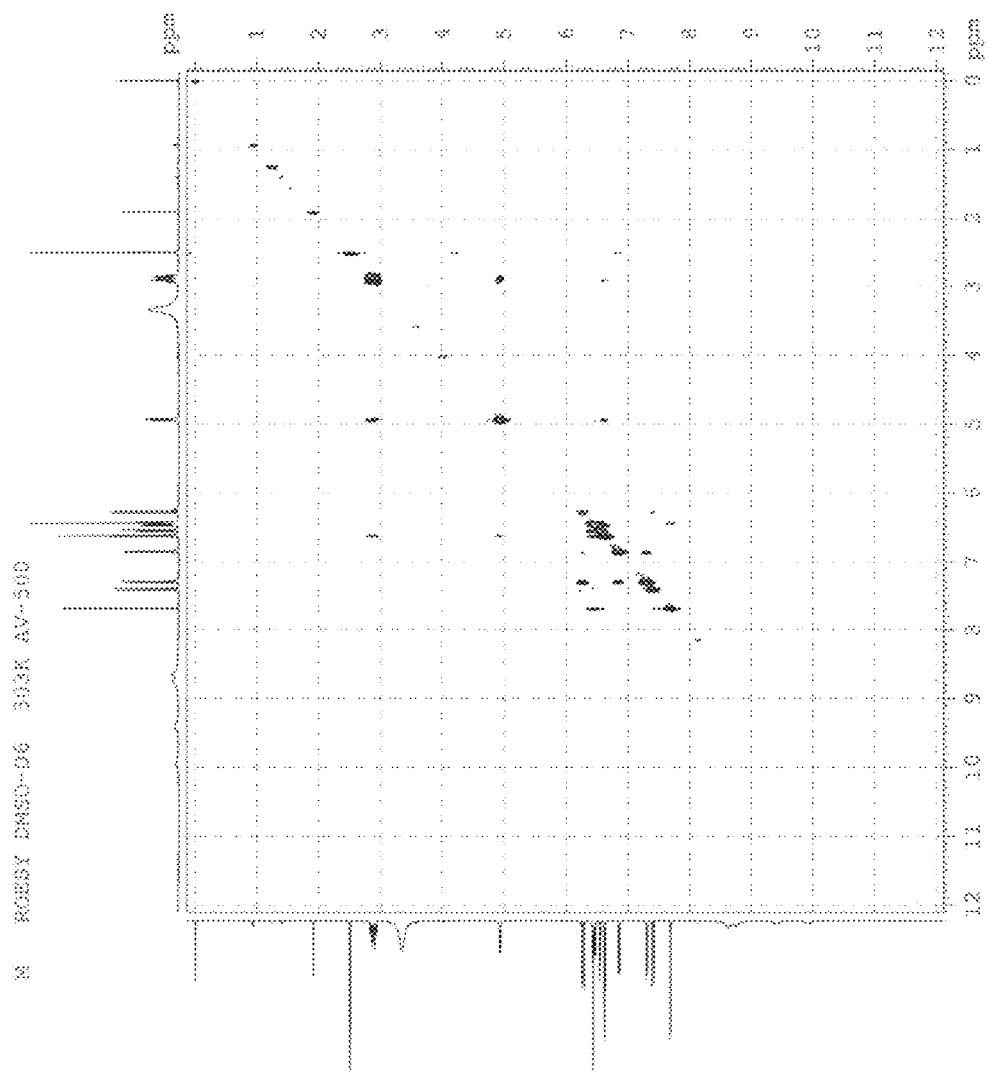
FIG. 6 was the ROESY figure of salvianolic acid T, A: (R)-salvianolic acid T; B: (S)-salvianolic acid T.
Figure 6B:
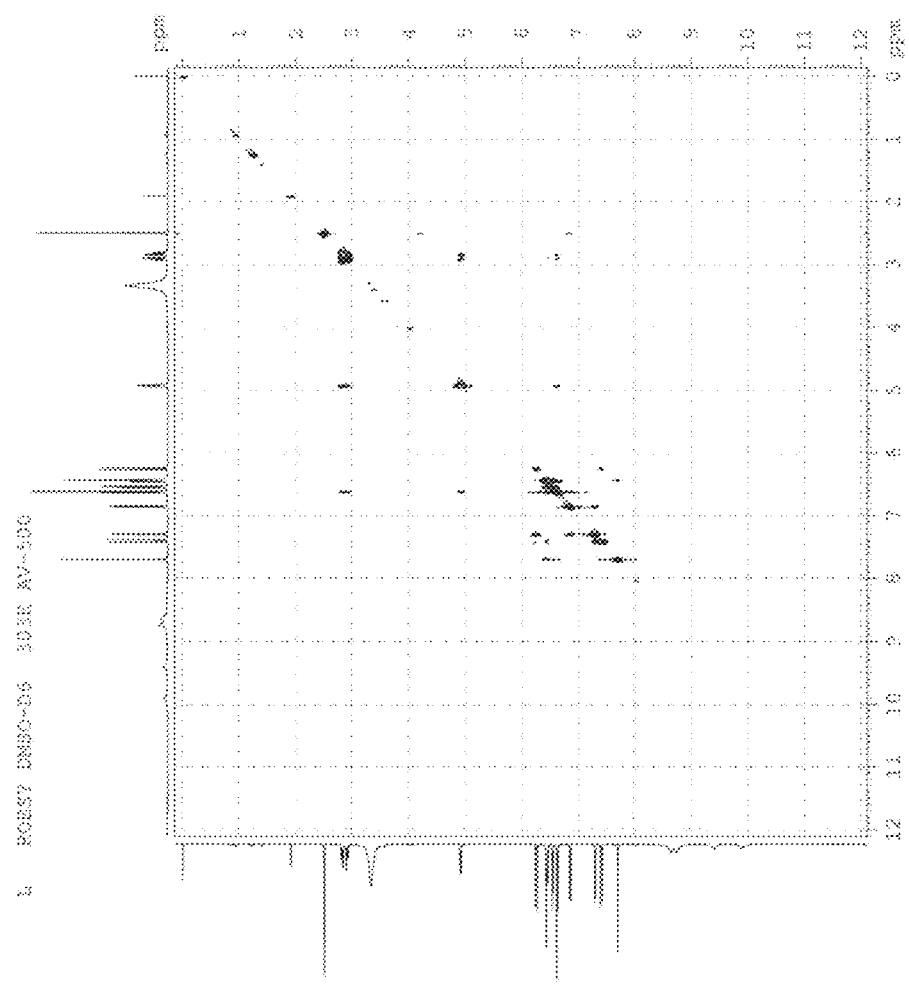
Figure 7A:
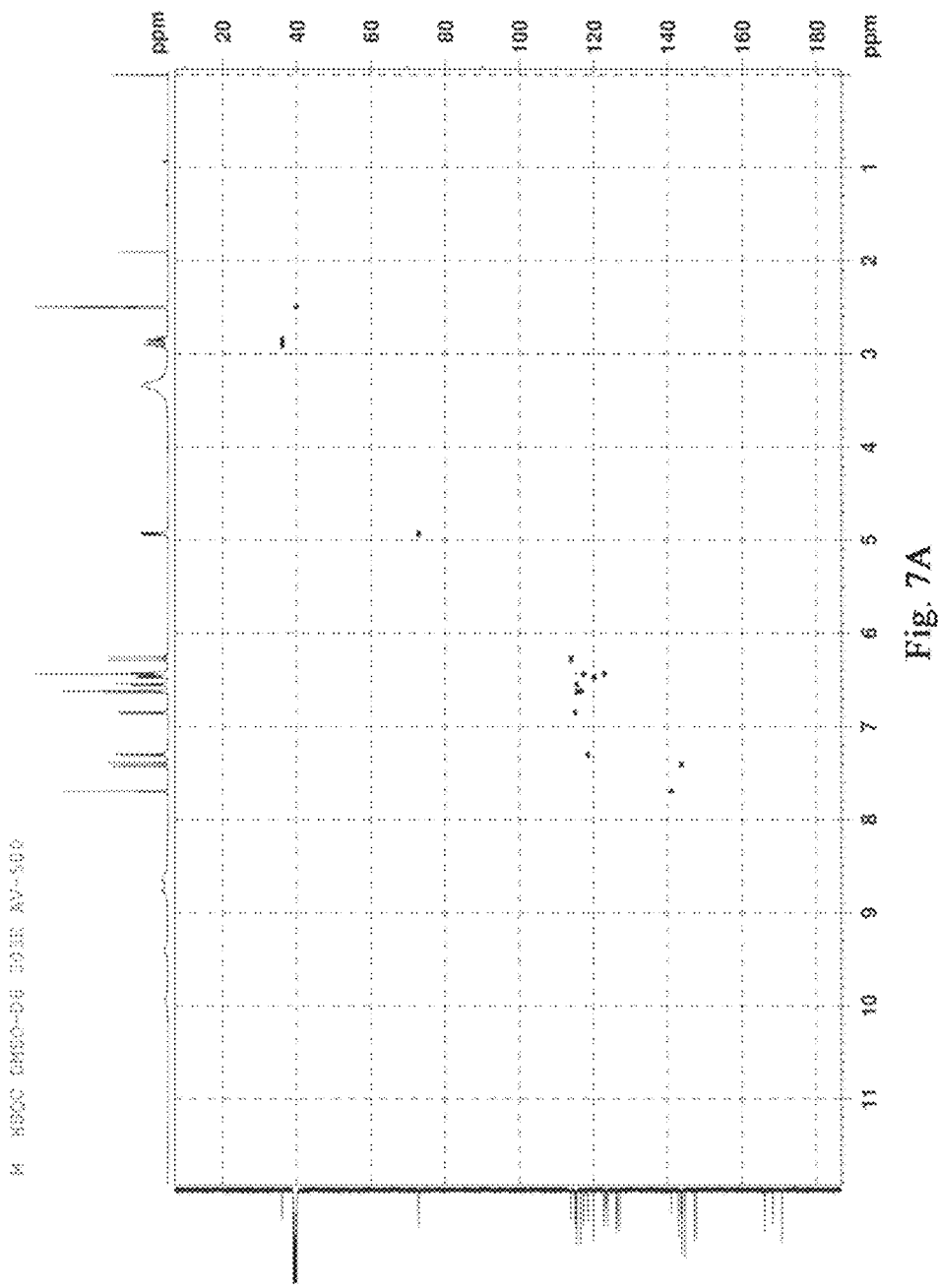
FIG. 7 was the HSQC figure of salvianolic acid T, A: (R)-salvianolic acid T; B: (S)-salvianolic acid T.
Figure 8A:
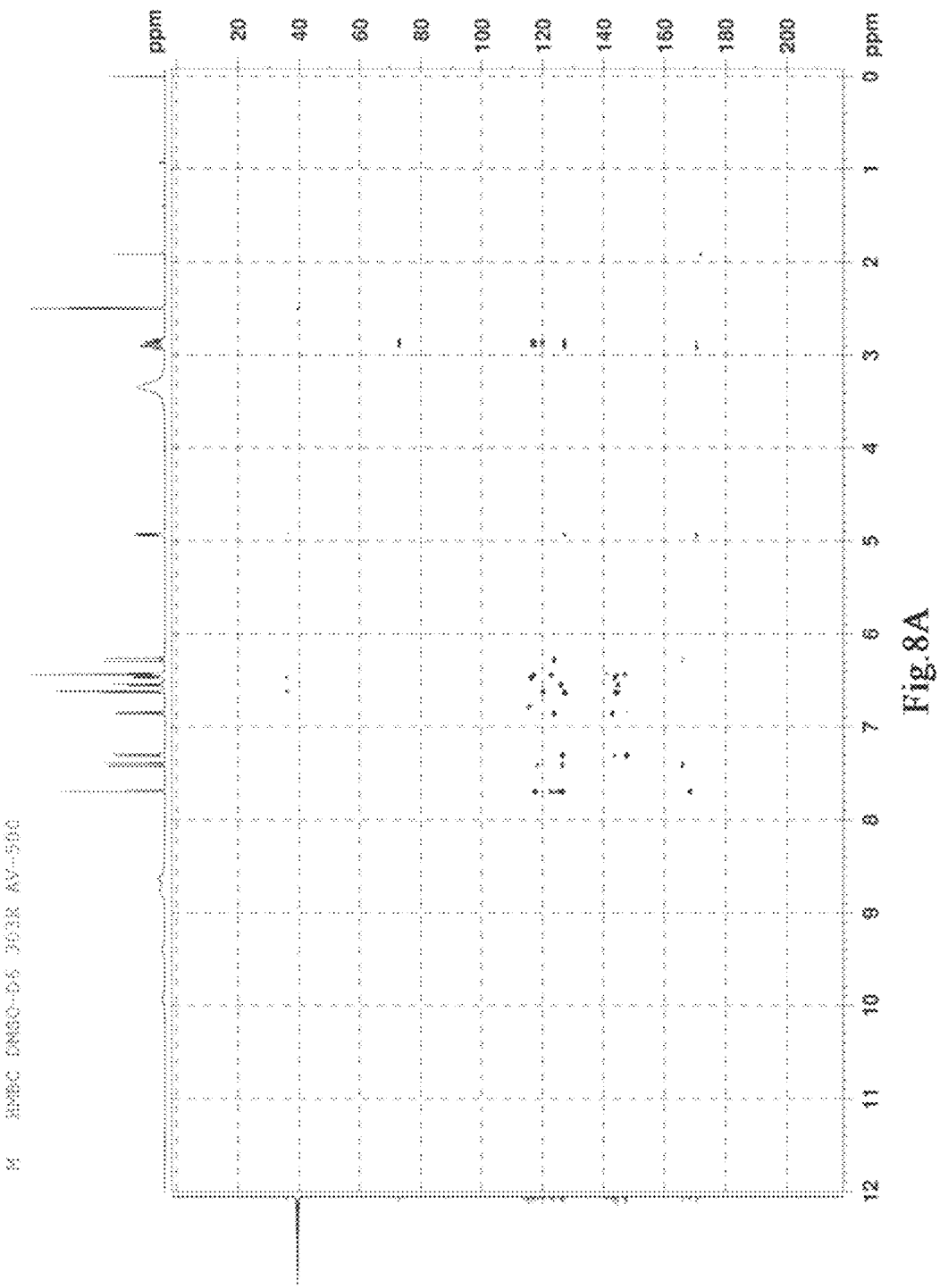
FIG. 8 was the HMBC figure of salvianolic acid T, A: (R)-salvianolic acid T; B: (S)-salvianolic acid T.
Figure 8D:
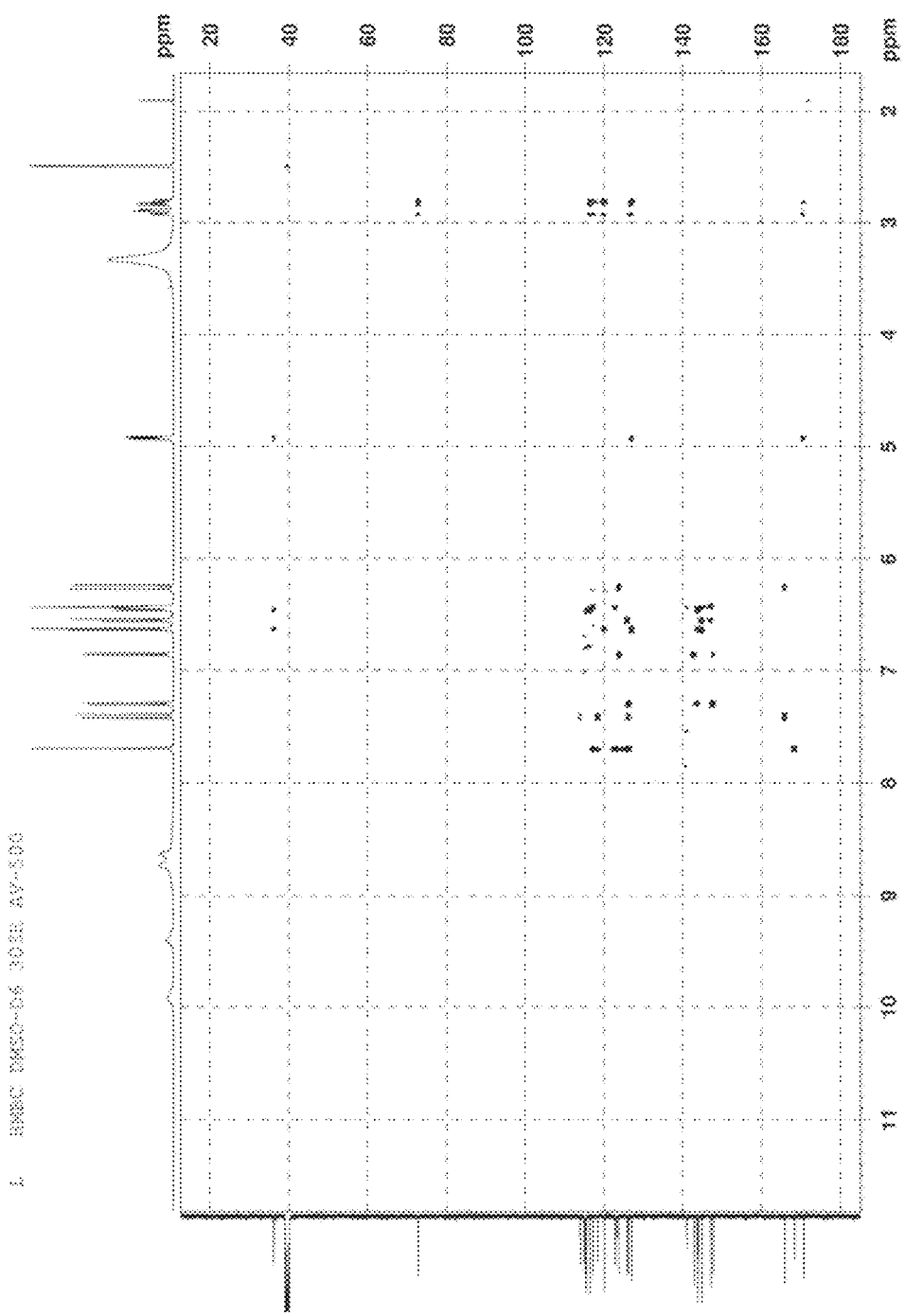
Figure 9A:
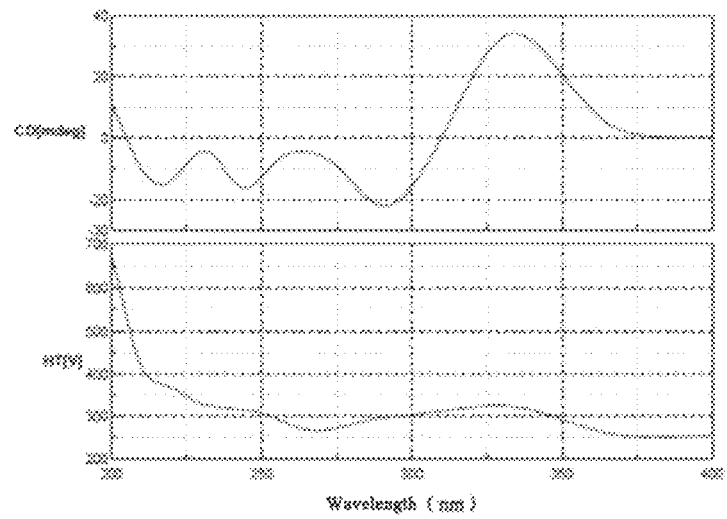
FIG. 9 was the CD figure of salvianolic acid T, A: (R)-salvianolic acid T; B: (S)-salvianolic acid T.
Figure 9B:
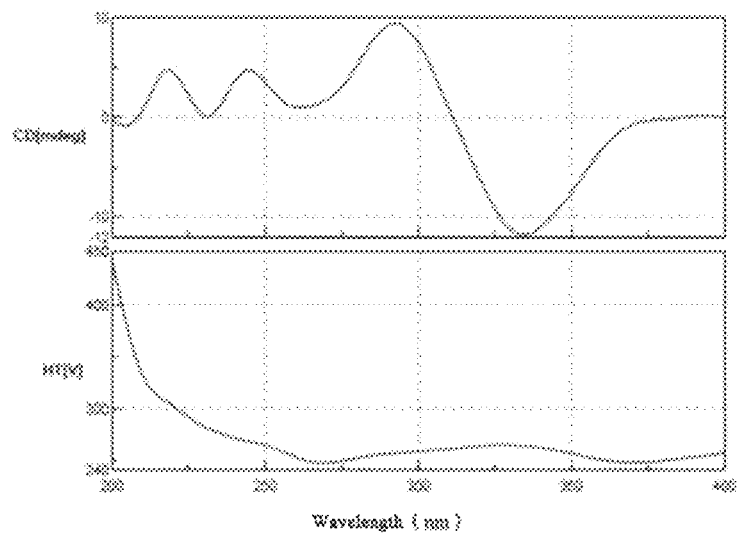
Figure 10A:
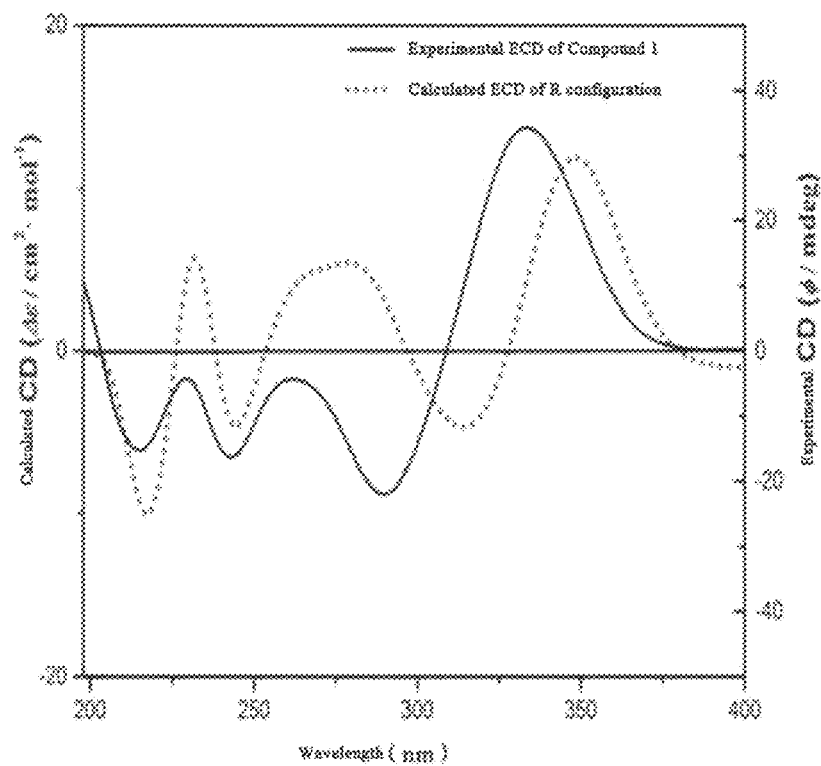
FIG. 10 was the comparison of CD figure and ECD simulated spectrum, A: (R)-salvianolic acid T; B: (S)-salvianolic acid T.
Figure 10B:
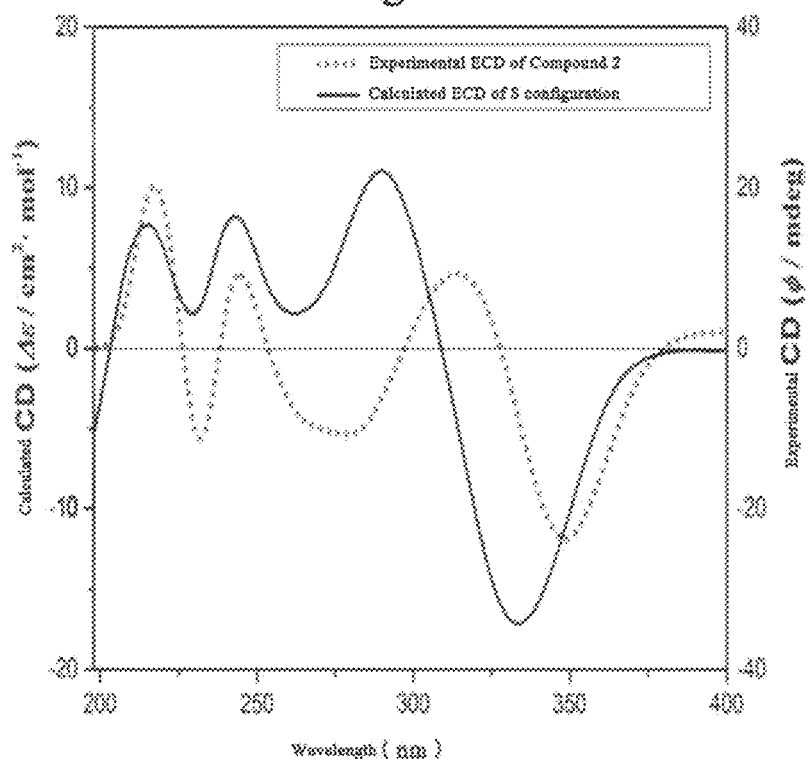

In an embodiment of this invention, the present invention provides a traditional Chinese medicine composition. Said composition is composed of following materials by weight percentage: 30%~80% of phenolic acid derivatives, 2%~10% of tanshinones and 15%~60% of saponines. Preferably, said composition is composed of following materials by weight percentage: 50%~70% of phenolic acid derivatives, 2%~6% of tanshinones and 25%~45% of saponines. Further preferably, said composition is composed of following materials by weight percentage: 66% of phenolic acid derivatives, 3% of tanshinones and 31% of saponines.

Said phenolic acid derivatives are composed of following ingredients by weight parts:

Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(2~6):(0.01~0.05):(1~3):(0.01~0.06):(0.5~2):(0.2~1):(0.05~0.3):(0.5~2):(0.2~1):(0.1~0.5):(0.1~0.5):(0.2~1).

Preferably, said phenolic acid derivatives are composed of following ingredients by weight parts:

Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54):(0.03~0.04):(0.86~1.13):(0.48~0.63):(0.12~0.16):(1~2):(0.44~0.58):(0.27~0.36):(0.29~0.38):(0.54~0.64).

Alternatively, said phenolic acid derivatives are composed of following ingredients by weight parts:

Danshensu:protocatechuic aldehyde:Salvianolic acid U+ Salvianolic acid T:Salvianolic D:Salvianolic acid G:rosmarinic acid:lithospermic acid:Salvianolic acid B:Salvianolic acid A=(3~5):(1~2):(0.5~2):(0.3~0.8):(0.1~0.5):(0.3~1.5):(0.1~0.3):(0.5~2):(0.5~1.5).

Preferably, said phenolic acid derivatives are composed of following ingredients by weight parts:

Danshensu:protocatechuic aldehyde:Salvianolic acid U+ Salvianolic acid T:Salvianolic D:Salvianolic acid G:rosmarinic acid:lithospermic acid:Salvianolic acid B:Salvianolic acid A=3.52:1.38:1.1:0.58:0.33:0.79:0.17:1.32:0.93.

In an embodiment of this invention, Salvianolic acid U+ Salvianolic acid T, yellowish powder, comes from the root of Salvia miltiorrhiza Bge. Preferably, Salvianolic acid U and Salvianolic acid T are used in combination, which is prepared by following method.

Extraction: the ground Salviae Miltiorrhizae crude medicine is decocted with water for 2 times; 2-hour extraction under alkaline condition for the first time and filtered; 1-hour extraction for the second time and filtered; the resultant filtrate is concentrated, cooled, added with alcohol and allowed to stand still to get the supernant that is then filtered and alcohol recovered to give the extract.

Salvianolic acid U+ Salvianolic acid T is separated by following method:

(a). The same volume of water is added into the alcohol-precipitation concentrated liquid, separated with the AB-8 macroporous adorption resin, eluted with water to collect the eluent;

(b). the pH value of eluent is adjusted, separated once again with the AB-8 macroporous adorption resin, eluted with acidified water and obtained eluent is removed. The resin is eluted with 50% ethanol to collect the eluent that is then concentrated to the dried extract;

(c). the dried extract is dissolved, separated with a polyamide column chromatography and eluted with 50% ethanol to collect the eluent that is then concentrated to the concentrated extract; and (d). the concentrated extract is dissolved, decolored with an MCI chromatographic column and eluted with 20% ethanol to collect the eluent, which is followed by concentration, lyophilization to give a mixture of Salvianolic acid U/T (purity of 95%).

Said Salvianolic acid U and Salvianolic acid T is resolved by following method:

The mixture of Salvianolic acid U/T is dissolved, applied on Sephadex LH-20 dextran gel column and eluted with 20% ethanol to collect fraction of Salvianolic acid U and Salvianolic acid T respectively by using HPLC to monitor. The eluent is concentrated to remove the ethanol completely, lyophilized to give the Salvianolic acid U and Salvianolic acid T respectively (purity of 90%).

In an embodiment of this invention, Danshensu, protocatechuic aldehyde, protocatechuic acid, caffeic acid, lithospermic acid, rosmarinic acid, Salvianolic B, Salvianolic acid A, Salvianolic acid G isomer, Salvianolic acid G and Salvianolic acid D are prepared by the method known in prior art. Aforesaid ingredients are used either in a state of single compound, reference standard, or by extracting and purifying traditional Chinese medicine. Purity of said ingredients is 90% or mores.

Preparation of Salvianolic Acid G Isomer:

C18 is used as a filling agent. The compound Salvia extract is dissolved with water, and water (0.02% formic acid) and acetonitrile (0.02% formic acid) are used as eluents A and B respectively to elute according to following gradient conditions:

|    | A water (0.02% formic acid) % | B acetonitrile (0.02% formic acid) % |
| --- | --- | --- |
| 0  | 90 | 10 |
| 15 | 80 | 20 |
| 25 | 75 | 25 |
| 30 | 74 | 26 |
| 45 | 54 | 46 |
| 50 | 48 | 52 |
| 62 | 28 | 72 |
| 70 | 0  | 100 |
| 76 | 0  | 100 |

The peak time of salvianolic acid G isomer on chromatogram is at about 30 min, and the eluent is collected, concentrated under reduced pressure and dried to give a single compound, the salvianolic acid G isomer with certain purity.

In an embodiment of this invention, said tanshinones are composed of following ingredients by weight parts:

Dihydrotanshinone I:tanshinone I:cryptotanshinone:tanshinone IIA:Danshenxinkun D=(0.01~0.05):(0.05~0.1): (0.02~0.1):(0.1~0.5):(0.1~0.5).

Preferably, said tanshinones are composed of following ingredients by weight parts:

Dihydrotanshinone I:tanshinone I:cryptotanshinone:tanshinone IIA:Danshenxinkun D=(0.02~0.03):(0.06~0.07): (0.04~0.06):(0.21~0.27):(0.22~0.28).

Alternatively, said tanshinones are composed of following ingredients by weight parts:

Dihydrotanshinone I:tanshinone I:cryptotanshinone:tanshinone IIA=(0.01~0.05):(0.05~0.1):(0.02~0.1):(0.1~0.5).

Preferably, said tanshinones are composed of following ingredients by weight parts:

Dihydrotanshinone I:tanshinone I:cryptotanshinone:tanshinone IIA=0.03:0.08:0.03:0.26.

In an embodiment of this invention, dihydrotanshinone I, tanshinone I, cryptotanshinone, tanshinone IIA and Danshenxinkun D are prepared by the method known in prior art. Aforesaid ingredients are used either in a state of single compound, reference standard, or by extracting and purifying traditional Chinese medicine. Purity of said ingredients is 90% or more.

In an embodiment of this invention, said saponines are composed of following ingredients by weight parts:

*Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.1~0.5):(1~4):(1~4):(0.2~0.7):(0.2~0.7).

Preferably, said saponines are composed of following ingredients by weight parts:

*Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.2~0.3):(1.9~3.0):(1.9~3.0): (0.48~0.51):(0.47~0.62).

In a preferred embodiment of this invention, said Ginsenoside Rg1, Re and Rh2 may exist simultaneously or in combination of two or more forms, and similarly, the Ginsenoside Rd or Rh1-R may exist simultaneously. Coexistence of Ginsenoside Rg1 and Re is preferred in a ratio of (16~17):1 by weight.

In an embodiment of this invention, said Ginsenoside Rg1 (or Re or Rh2), Ginsenoside Rb1, Ginsenoside Rh1-S and Ginsenoside Rd (or Rh1-R) are prepared by the method known in prior art. Aforesaid ingredients are used either in a state of single compound, reference standard, or by extracting and purifying traditional Chinese medicine. Purity of said ingredients is 90% or more.

In an embodiment of this invention, the structure of new compound of salvianolic acid was identified by physicochemical properties, high resolution mass spectrometry (QFT-ESI), electrospray ionization mass spectrometry (ESI-MS), $^1$H-NMR, $^{13}$C-NMR, DEPT, COSY, HMBC, HMQC and CD (FIG. 1~10).

The present invention relates to a new compound represented by the general formula (I) as follows:

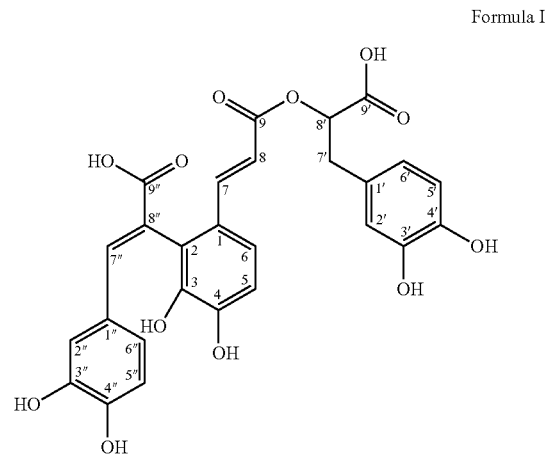

Formula I $^1$H-NMR shows 1 signal of methenyl proton attached to oxygen at δ 4.93 (1H, dd, 8.0, 4.5 Hz); 11 signals of aromatic proton at δ 6.85 (1H, d, 8.5 Hz), δ 7.31 (1H, d, 8.5 Hz), δ 7.41 (1H, d, 15.5 Hz), δ 6.27 (1H, d, 15.5 Hz), δ 6.62 (1H, s), δ 6.63 (1H, d, 8.0 Hz), δ 6.47 (1H, d, 8.0 Hz), δ 6.44 (1H, d, 2.0 Hz), δ 6.55 (1H, d, 8.5 Hz), δ 6.43 (1H, dd, 8.5, 2.0 Hz), δ 7.69 (1H, s); 2 signals of aliphatic proton at δ 2.89 (2H, ddd, 14.0, 8.0, 4.5 Hz).

Carbon-13 nuclear magnetic resonance $^{13}$C-NMR spectrum shows 27 carbon signals, including 1 aliphatic carbon signal at δ 36.0, 1 signal of methenyl carbon attached to oxygen at δ 72.8, 3 signals of carbonyl carbon at δ 166.0, δ 170.6, δ 168.4, and 22 signals of double-bond carbon at δ 123.7, δ 126.4, δ 142.9, δ 147.7, δ 115.0, δ 118.4, δ 143.7, δ 113.9, δ 127.1, δ 116.5, δ 143.9, δ 144.8, δ 115.5, δ 120.0, δ 126.0, δ 117.3, δ 144.8, δ 147.2, δ 115.3, δ 122.9, δ 141.1, δ 123.4.

In an embodiment of this invention, said compound of the present invention has 2 isomers with optical rotation respectively at −157.5° and 196.6°. Compound with C-8' absolute configuration set as S/R-configuration is obtained through molecular optimum design and calculated by BPV86 method having TD-SCF with (2d, p) basis sets to read comparison between result and experimental CD spectrum of the compound. It is inferred by the substantially matched CD spectra that the absolute configuration of C-8' in 2 isomoers of the compound of the present invention are S configuration and R configuration (see FIG. 10). The spectrum by HMBC of the compound in the present invention is presented as follows:

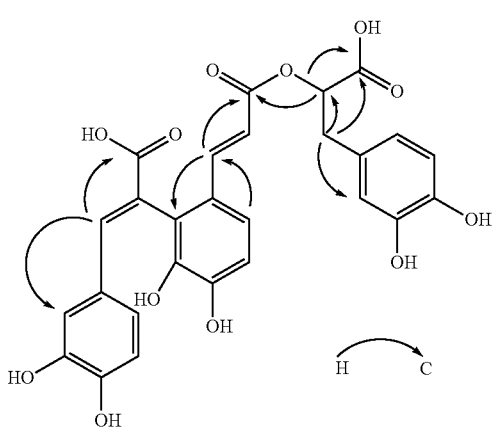

Said salvianolic acid T is prepared by following method:

a) extraction: extracting *Salviae Miltiorrhizae* crude drug or a mixture of *Salviae Miltiorrhizae* and other crude drugs with water and filtering, concentrating the filtrate, adding alcohol to precipitate and obtain a supernatant, then concentrating the supernatant to obtain an extract;

b) separation: dissolving the extract of the step a) in water, applying on the macroporous absorbent resin, eluting the resin with acidic solution to remove the impurities and then eluting with ethanol to obtain an ethanol eluent, concentrating the ethanol eluent to obtain an extract;

c) purification: purifying the extract of the step b) with high-pressure preparative LC; stationary phase is C18 reversed-phase silica column; mobile phase is acetonitrile-water-formic acid by isocratic elution or gradient elution method with detective wavelength at 280 nm; HPLC is used to monitor the process of elution to collect the eluent containing the salvianolic acid T; after being concentrated, the salvianolic acid T is obtained.

In an embodiment of this invention, the preparation of said traditional Chinese medicine composition is provided. In a preferred embodiment, said traditional Chinese medicine composition may account for 0.1~99.9 wt % of said preparation, and the balanced is pharmaceutically acceptable carrier. In another embodiment of this invention, the composition is prepared in the form of unit dosage and said unit dosage refers to individual preparation, e.g. each tablet of tablets, each capsule of capsules, each bottle of oral solutions and each bag of granules etc.

In an embodiment of this invention, the preparation of said traditional Chinese medicine composition is suitable for administrating orally, parenterally (including subcutaneously e.g. the injection or the reservoir-type tablet; intradermally; intrathecally; intramuscularly e.g. the reservoir and intravenously), rectally and topically (e.g. sublingually). The most suitable administration route, however, depends on the condition of patients.

In an embodiment of this invention, said carriers refer to various kinds of organic or inorganic carriers that are administrated jointly with the composition of traditional Chinese medicine, for example the excipients used for solid preparation, the lubricant, the adhesive, the disintegrant agent and coating agent, or pharmaceutical additive, for example the colorant agent and sweetening agent. Said carriers are selected from: sugar alcohol, e.g. mannitol, sorbitol, xylitol; amino acid, e.g. cysteine hydrochloride, methionine, glycine; Vitamin C; EDTA disodium, EDTA calcium disodium salt; inorganic salt, e.g. monovalent alkali carbonate, acetate, phosphate or its aqueous solution, sodium chloride, potassium chloride, sodium pyrosulfite, sodium bisulfite, sodium thiosulfate; calcium carbonate, calcium bicarbonate; stearate, e.g. calcium stearate, magnesium stearate; inorganic acid, e.g. hydrochloride, sulfuric acid, phosphoric acid; acetic acid; organic acid salt, e.g. sodium lactate; oligosaccharide, polysaccharide, cellulose and its derivatives, e.g. maltose, glucose, fructose, dextran, sucrose, lactose, cyclodextrin (such as β-cyclodextrin), starch; silicon derivative; alginate; gelatin; PVP, glycerol; agar gel; surfactant, e.g. Tween-80; PEG; phospholipids; Kaolin; talcum powder etc.

In an embodiment of this invention, said composition can be prepared in any pharmaceutically acceptable dosage form, including the tablet such as sugar-coated tablet, film-coated tablet and enteric-coated tablet, the capsule such as soft capsule and hard capsule, the oral liquid solution, the buccal tablet, the granules, the instant powder, the pill, the pulvis, the paste such as ointment and paster, the Dan, the suspension, the powder, the solution, the injection, the suppository, the cream, the ointment, the plaste, the spray, the drop, the drop pill and the patch, preferably the orally-administrated dosage form, such as the capsule, the tablet, the oral solution, the granule, the pill, the powder, the Dan and the ointment etc., also preferably the injection, such as the powder injection, injection liquid, infusion etc. In the present invention, the tablet is the most preferable.

In an embodiment of this invention, said orally-administrated dosage form can include commonly used excipients, adhesive, filling agent, diluent, tableting agent, lubricant, disintegrating agent, colorant agent, flavoring agent, wetting agent. If necessary, the tablet may be coated.

Suitable examples of said filling agent include the cellulose, mannitol, lactose and other analogous filling agent.

Preferable examples of said excipient include the lactose, the D-mannitol, the D-sorbitol, the starch, e.g. the α-starch, the dextrin, the crystalline cellulose, the low-substituted hydroxy propyl cellulose (HPC), the sodium carboxymethyl cellulose, the Arabic gum, the amylopectin starch, the light anhydrous silicic acid, the synthetic aluminum silicate and aluminium magnesium silicate etc.

Preferable examples said lubricant include the magnesium stearate, the calcium stearate, the talc, the silica gel and the sodium dodecyl sulfate etc.

Preferable examples of said adhesive include the α-starch, the lactose, the gelatin, the Arabic gum, the methyl cellulose, the carboxymethyl cellulose, the sodium carboxymethyl cellulose, the crystalline cellulose, the sugar, the D-mannitol, the trehalose, the dextrin, the amylopectin starch, the HPC, the HPMC and the pyrrolidone.

Preferable examples of said disintegrating agent includes the lactose, the sugar, the starch, the carboxymethyl cellulose, the calcium carboxymethyl cellulose, the sodium aminoalkyl, the sodium carboxymethyl cellulose, the light anhydrous silicic acid, the low-substituted HPC, the starch, the PVP and the sodium starch glycollate.

Preferable examples of said coating agent include the HPMC, the HPC, the ethyl cellulose, the carboxymethyl cellulose and the polyvinyl alcohol (PVA).

Preferable examples of said colorant agent include water-soluble edible tartrazine dye (food dye such as edible red No. 2 and No. 3, edible yellow No. 4 and No. 5, edible blue No. 1 and No. 2); water-insoluble lake colors (such as aluminum salt of the afore-mentioned water-soluble edible tartrazine dye) and natural dye (such as β-carotene, chlorophyll and colcothar) etc.

Preferable examples of said flavoring agent include saccharin sodium, glycyrrhetinic acid, aspartame and stevioside etc.

Conventional method for preparing tablets comprises combining the traditional Chinese medicine composition of the present invention with one or more kinds of pharmaceutically acceptable vehicle, and then having the same pressed or molded.

The composition of the present invention can also be formulated into oral liquid preparations, for instance, water-soluble or oil-soluble suspensions, solutions, emulsions, syrups, etc. The traditional Chinese medicine composition of the present invention can also be prepared into a dry product, re-blended with water or other suitable carriers before use. This sort of liquid preparations can contain conventional additives, including suspending-agent, such as sorbitol syrup, methylcellulose, glucose/syrup, gelatin, hydroxyethyl cellulose, carboxymethyl cellulose, aluminum stearate gel or hydrogenated edible fat; emulsifying-agent, such as lecithin, sorbitan monoleate or arabic gum; non-aqueous carrier (including edible oil), such as almond oil, fractionated coconut oil, butyraceous ester, propylene glycol or ethanol; as well as preservative, such as methyl paraben, nipasol and sorbic acid. The conventional flavoring agent or colorant agent, if necessary, can be included.

Parenterally-administered preparations include aqueous and non-aqueous sterile injections, wherein, optionally, these preparations can contain antioxidant, buffering agent, bacteriostatic agent and isotonic agent etc; and the parenterally-administered preparations can include aqueous and non-aqueous sterile suspensions, wherein, optionally, these preparations can contain suspending-agent and thickening agent. Said preparations can be preserved in a single-dose or multi-dose vessel such as sealed ampoules and vials, which can be stored under the freeze drying condition and re-constituted before use with sterile liquid carrier, for example the injectable water.

Rectally-administered preparations can be suppositories containing conventional suppository base, for example, cocoa butter, stearic acid or other glycerides or ethylene glycol.

Oral cavity topically-administered preparations, for example the buccal or sublingual preparations, include troches, wherein the active ingredient is embedded in a flavored base such as the sucrose and arabic gum; also pastilles, wherein the active ingredient is embedded in a base such as the gelatin and glycerol, or the sucrose and Arabic gum.

The composition of the present invention can also be formulated into reservoir-type preparations, and such a sustained-release preparation can be administered by implantation (such as subcutaneous implantation or intramuscular implantation) or intramuscular injection. Therefore, the traditional Chinese medicine composition of the present invention can be prepared with suitable polymers, hydrophobic materials (for example the emulsion in acceptable oil), or ion-exchange resins, or prepared into a slightly-soluble derivatives, for example the slightly-soluble salt.

In an embodiment of this invention, the composition of present invention has a therapeutic effect on cardiovascular system, in particular on diluting coronary artery, inhibiting platelet aggregation, inhibiting thrombosis and anti acute myocardial infarction.

EMBODIMENTS

The following examples are offered for the purpose of elaborate explanation of the present invention only and are not intended to limit the scope of the invention in any way.

Example 1

66 g of phenolic acid derivatives, 3 g of tanshinones and 31 g of saponines were mixed uniformly to prepare the composition of the present invention. Wherein, the active pharmaceutical ingredients (API) were present as follows: 27 g of Danshensu, 0.16 g of protocatechuic acid, 9.30 g of protocatechuic aldehyde, 0.24 g of caffeic acid, 6.84 g of Salvianolic acid U+Salvianolic acid T, 3.6 g of rosmarinic acid, 0.9 g of lithospermic acid, 5.88 g of Salvianolic acid B, 3.5 g of Salvianolic acid A, 2.14 g of Salvianolic acid G isomer, 2.31 g of Salvianolic acid G, 4.29 g of Salvianolic acid D, 0.1 g of dihydrotanshinone I, 0.33 g of tanshinone I, 0.22 g of cryptotanshinone, 1.14 g of tanshinone IIA, 1.14 g of Danshenxinkun D, 12.38 g of Ginsenoside Rg1, Re or Rh2, 12.38 g of Ginsenoside Rb1, 3.12 g of Ginsenoside Rh1-S, 3.06 g of Ginsenoside Rd or Rh1-R and 2.29 g of *Panax Notoginseng* Saponin R1.

Example 2

62 g of phenolic acid derivatives, 4 g of tanshinones and 34 g of saponines were mixed uniformly to prepare the composition of the present invention. Wherein, the active pharmaceutical ingredients (API) were present as follows: 26.5 g of Danshensu, 0.17 g of protocatechuic acid, 8.47 g of protocatechuic aldehyde, 0.22 g of caffeic acid, 6.22 g of Salvianolic acid U+ Salvianolic acid T, 3.47 g of rosmarinic acid, 0.88 g of lithospermic acid, 5.39 g of Salvianolic acid B, 3.19 g of Salvianolic acid A, 1.98 g of Salvianolic acid G isomer, 2.09 g of Salvianolic acid G; 3.52 g of Salvianolic acid D, 0.17 g of dihydrotanshinone I, 0.39 g of tanshinone I, 0.34 g of cryptotanshinone, 1.52 g of tanshinone IIA, 1.56 g of Danshenxinkun D, 23.5 g of Ginsenoside Rg1+Re, 23.5 g of Ginsenoside Rb1, 4.79 g of Ginsenoside Rh1-S, 5.83 g of Ginsenoside Rd or Rh1-R and 4.36 g of *Panax Notoginseng* Saponin R1.

Example 3

62 g of phenolic acid derivatives, 4 g of tanshinones and 34 g of saponines were mixed uniformly to prepare the composition of the present invention. Wherein, the active pharmaceutical ingredients (API) were present as follows: 25 g of Danshensu, 1.25 g of protocatechuic acid, 12.5 g of protocatechuic aldehyde, 1.25 g of caffeic acid, 6.25 g of Salvianolic acid U+ Salvianolic acid T, 2.5 g of rosmarinic acid, 0.625 g of lithospermic acid, 6.25 g of Salvianolic acid B, 2.5 g of Salvianolic acid A, 1.25 g of Salvianolic acid G isomer, 0.125 g of Salvianolic acid G 2.5 g of Salvianolic acid D, 0.14 g of dihydrotanshinone I, 0.7 g of tanshinone I, 0.28 g of cryptotanshinone, 1.4 g of tanshinone IIA, 1.4 g of Danshenxinkun D, 14.17 g of Ginsenoside Rg1+Re, 14.17 g of Ginsenoside Rb1, 2.83 g of Ginsenoside Rh1-S, 2.83 g of Ginsenoside Rd or Rh1-R and 2.62 g of *Panax Notoginseng* Saponin R1.

Example 4

62 g of phenolic acid derivatives, 4 g of tanshinones and 34 g of saponines were mixed uniformly to prepare the composition of the present invention. Wherein, said phenolic acid derivatives comprised following ingredients by weight parts: Danshensu:protocatechuic acid:protocatechuic aldehyde:caffeic acid:Salvianolic acid U+ Salvianolic acid T:rosmarinic acid:lithospermic acid: Salvianolic acid B:Salvianolic acid A:Salvianolic acid G isomer:Salvianolic acid G:Salvianolic D=(2~6):(0.01~0.05):(1~3):(0.01~0.06):(0.5~2):(0.2~1):(0.05~0.3):(0.5~2):(0.2~1):(0.1~0.5):(0.1~0.5):(0.2~1); said tanshinones comprised following ingredients by weight parts: Dihydrotanshinone I:tanshinone I:cryptotanshinone:tanshinone IIA:Danshenxinkun D=(0.01~0.05):(0.05~0.1):(0.02~0.1):(0.1~0.5):(0.1~0.5); said saponines comprised following ingredients by weight parts: *Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.1~0.5):(1~4):(1~4):(0.2~0.7):(0.2~0.7).

Example 5

30 g of phenolic acid derivatives, 10 g of tanshinones and 60 g of saponines were mixed uniformly to prepare the composition of the present invention. Wherein, said phenolic acid derivatives comprised following ingredients by weight parts: Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(2~6):(0.01~0.05):(1~3):(0.01~0.06):(0.5~2):(0.2~1):(0.05~0.3):(0.5~2):(0.2~1):(0.1~0.5):(0.1~0.5):(0.2~1); said tanshinones comprised following ingredients by weight parts: Dihydrotanshinone I:tanshinone I:cryptotanshinone:tanshinone IIA:Danshenxinkun D=(0.01~0.05):(0.05~0.1): (0.02~0.1):(0.1~0.5):(0.1~0.5); said saponines comprised following ingredients by weight parts: *Panax Notoginseng* Saponin R1:Ginsenoside Rg1 or Re or Rh2:Ginsenoside Rb1:Ginsenoside Rh1-S:Ginsenoside Rd or Rh1-R=(0.1~0.5):(1~4):(1~4):(0.2~0.7):(0.2~0.7).

Example 6

80 g of phenolic acid derivatives, 5 g of tanshinones and 15 g of saponines were mixed uniformly to prepare the composition of the present invention. Wherein, said phenolic acid derivatives comprised following ingredients by weight parts: Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54):(0.03~0.04):(0.86~1.13):(0.48~0.63):(0.12~0.16):(0.74~0.98):(0.44~0.58):(0.27~0.36):(0.29~0.38):(0.54~0.64); said tanshinones comprised following ingredients by weight parts: Dihydrotanshinone I:tanshinone I:cryptotanshinone:tanshinone IIA:Danshenxinkun D=(0.02~0.03):(0.06~0.07):(0.04~0.06):(0.21~0.27):(0.22~0.28); said saponines comprised following ingredients by weight parts: *Panax Notoginseng* Saponin R1:Ginsenoside Rg1 (or Re or Rh2):Ginsenoside Rb1:Ginsenoside Rh1-S:Ginsenoside Rd (or Rh1-R)=(0.2~0.3):(1.9~3.0):(1.9~3.0):(0.48~0.51):(0.47~0.62).

Example 7

70 g of phenolic acid derivatives, 2 g of tanshinones and 28 g of saponines were mixed uniformly to prepare the composition of the present invention. Wherein, said phenolic acid derivatives comprised following ingredients by weight parts: Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54):(0.03~0.04):(0.86~1.13):(0.48~0.63):(0.12~0.16):(0.74~0.98):(0.44~0.58):(0.27~0.36):(0.29~0.38):(0.54~0.64); said tanshinones comprised following ingredients by weight parts: Dihydrotanshinone I:tanshinone I:cryptotanshinone:tanshinone IIA:Danshenxinkun D=(0.02~0.03):(0.06~0.07):(0.04~0.06):(0.21~0.27):(0.22~0.28); said saponines comprised following ingredients by weight parts: *Panax Notoginseng* Saponin R1:Ginsenoside Rg1 (or Re or Rh2):Ginsenoside Rb1:Ginsenoside Rh1-S:Ginsenoside Rd (or Rh1-R)=(0.2~0.3):(1.9~3.0):(1.9~3.0):(0.48~0.51):(0.47~0.62).

Example 8

50 g of phenolic acid derivatives, 10 g of tanshinones and 40 g of saponines were mixed uniformly to prepare the composition of the present invention.

Example 9

50 g of phenolic acid derivatives, 6 g of tanshinones and 44 g of saponines were mixed uniformly to prepare the composition of the present invention.

Example 10

69 g of phenolic acid derivatives, 6 g of tanshinones and 25 g of saponines were mixed uniformly to prepare the composition of the present invention. Wherein, said phenolic acid derivatives comprised following ingredients by weight parts: Danshensu:protocatechuic acid:protocatechuic aldehyde:caffeic acid:Salvianolic acid U+ Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54):(0.03~0.04):(0.86~1.13):(0.48~0.63):(0.12~0.16):(0.74~0.98):(0.44~0.58):(0.27~0.36):(0.29~0.38):(0.54~0.64); said tanshinones comprised following ingredients by weight parts: Dihydrotanshinone I:tanshinone I:cryptotanshinone:tanshinone IIA:Danshenxinkun D=(0.02~0.03):(0.06~0.07):(0.04~0.06):(0.21~0.27):(0.22~0.28); said saponines comprised following ingredients by weight parts: *Panax Notoginseng* Saponin R1:Ginsenoside Rg1 (or Re or Rh2):Ginsenoside Rb1:Ginsenoside Rh1-S:Ginsenoside Rd (or Rh1-R)=(0.2~0.3):(1.9~3.0):(1.9~3.0):(0.48~0.51):(0.47~0.62).

Preparation of Traditional Chinese Medicine Composition

Example 11

0.5 g of the traditional Chinese medicine composition of Example 1 and 10.5 g of PEG-6000 were mixed uniformly, molten by heating and transferred to a dropping tank. The liquid was dropped into a liquid paraffin at 6~8° C. to give 400 drop pills after removing the remaining paraffin.

Example 12

0.5 g of the traditional Chinese medicine composition of Example 2, 4.5 g of glucose, 0.9 g of sodium thiosulfate and 1 ml of distilled water were mixed uniformly, lyophilized and loaded separately to give 500 lyophilized powders for injection.

Example 13

0.5 g of the traditional Chinese medicine composition of Example 2, 5.5 g of mannitol, 0.9 g of EDTA calcium disodium salt and 2 ml of distilled water were mixed uniformly, lyophilized and loaded separately to give 300 lyophilized powders for injection.

Example 14

0.5 g of the traditional Chinese medicine composition of Example 2, 50 g of starch and 50 g of sucrose were mixed uniformly, granulated and tableted to give tablets.

Example 15

0.5 g of the traditional Chinese medicine composition of Example 2, 50 g of starch and 50 g of sucrose were mixed uniformly, granulated and loaded into the capsule to give capsules.

Preparation of Salvianolic Acid T, (S)-Salvianolic Acid T and (R)-Salvianolic Acid T

Example 16

*Salvia Militiorrhiza* was transferred to an herbal decocting pot, into which 6 times of 0.3% (w/v) sodium bicarbonate aqueous solution based on the amount of *Salvia Militiorrhiza* was added, decocted for 2.5 h and filtered to give the filtrate. The filtrate was concentrated to obtain the aqueous extract with relative density of 1.22 (80° C.).

The aqueous extract was added with 95% (v/v) ethanol to make the final ethanol content as 60% (v/v) (25° C.) and allowed to stand still for 24 h to give the supernatant. The supernatant was concentrated under reduced pressure to obtain the ethanol-precipitated extract with a relative density of 1.32 (60° C.).

The ethanol-precipitated extract was dissolved with water, passed through AB-8 macroporous resin column and eluted with aqueous hydrochloric acid solution (pH=3.0) until the eluent was nearly colorless. Later, 5 times of 95% (v/v) ethanol based on the column volume was used to elute the column and the eluent was concentrated to give the extract with no smell of alcohol.

The extract obtained from previous step was dissolved with mobile phase (acetonitrile:water:formic acid=15:85:1 by volume) and purified with NOVASEP LC80-600 dynamic axial high-pressure preparative LC. C18 reverse-phase chromatographic column (10 μm, YMC Inc.) was used as stationary phase to carry out the isocratic elution with the mobile phase of acetonitrile:water:formic acid=15:85:1 by volume. The flow rate was at 300 mL/min and detective wavelength at 280 nm. The process of elution was monitored by using HPLC to collect the fraction between 21.2~24.0 min and concentrate to dry with the rotary evaporator to obtain salvianolic acid T.

Afore-obtained salvianolic acid T was dissolved with mobile phase (acetonitrile:water:formic acid=17:83:1 by volume) and Waters Prep 400 preparative LC was used to carry out chiral isomer separation. The chromatographic column was CHIRALCEL® OD-RH reverse-phase chiral column (250×20 mm, 5 μm) and the mobile phase of acetonitrile:water:formic acid=17:83:1 by volume was used to perform isocratic elution. The flow rate was at 25 mL/min and detective wavelength at 280 nm. The process of elution was monitored by using HPLC to collect the fraction of (S)-salvianolic acid T between retention time of 19.5~21.1 min and (R)-salvianolic acid T between retention time of 23.9~25.3 min. The eluent was concentrated with rotary evaporator at 30° C. and lyophilized to obtain the pure product of (S)- and (R)-salvianolic acid T.

By using a high-resolution mass spectrometry, a quasi-molecular ion peak of (S)-salvianolic acid T was at m/z 537.1033 and (R)-salvianolic acid T at m/z 537.1032.

NMR data assignments for (S)-salvianolic acid T and (R)-salvianolic acid T were seen in the following tables.

TABLE 1

$^1$H (DMSO, J Hz) data assignment for the (R)-salvianolic acid T

| No. | $\delta_H$ | $\Delta c$ | $^1$H-$^1$H COSY | HMBC |
|---|---|---|---|---|
| 1 | — | 123.7 | | H-5, H-8 |
| 2 | — | 126.4 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.31 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 113.9 | H-7 | H-7 |
| 9 | — | 166.0 | | H-7, H-8, H-8' |
| 1' | — | 127.1 | | H-2', H-5', H-8', H-7' |
| 2' | 6.62 (1H, s) | 116.5 | H-6' | H-6' |
| 3' | — | 143.9 | | H-2', H-5' |
| 4' | — | 144.8 | | H-2', H-5', H-6' |
| 5' | 6.63 (1H, d, 8.0 Hz) | 115.5 | H-6' | H-6' |
| 6' | 6.47 (1H, d, 8.0 Hz) | 120.0 | H-2', 5' | H-2', H-5' |
| 7' | 2.89 (2H, ddd, 14.0, 8.0, 4.5 Hz) | 36.0 | H-8' | H-2', H-5', H-6', H-8' |
| 8' | 4.93 (1H, dd, 8.0, 4.5 Hz) | 72.8 | H-7' | H-7' |
| 9' | — | 170.6 | | H-7', H-8' |
| 1" | — | 126.0 | | H-2" |
| 2" | 6.44 (1H, d, 2.0 Hz) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 8.5 Hz) | 115.3 | H-6" | |
| 6" | 6.43 (1H, dd, 8.5, 2.0 Hz) | 122.9 | H-2", 5" | H-2", H-7" |
| 7" | 7.69 (1H, s) | 141.1 | | H-6" |
| 8" | — | 123.4 | | H-7" |
| 9" | — | 168.4 | | H-7" |

TABLE 2

$^1$H (DMSO, J Hz) data assignment for the (S)-salvianolic acid T

| No. | $\delta_H$ | $\Delta c$ | $^1$H-$^1$H COSY | HMBC |
|---|---|---|---|---|
| 1 | — | 123.8 | | H-5, H-8 |
| 2 | — | 126.3 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.29 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 114.0 | H-7 | H-7 |
| 9 | — | 165.9 | | H-7, H-8, H-8' |
| 1' | — | 127.2 | | H-2', H-5', H-8', H-7' |
| 2' | 6.62 (1H, s) | 116.5 | H-6' | H-6', H-7' |
| 3' | — | 143.9 | | H-2', H-5', H-6' |
| 4' | — | 144.9 | | H-2', H-5' |
| 5' | 6.63 (1H, d, 8.0 Hz) | 115.5 | H-6' | |

TABLE 2-continued 1H (DMSO, J Hz) data assignment for the (S)-salvianolic acid T

| No. | $\delta_H$ | $\Delta c$ | 1H-1H COSY | HMBC |
|---|---|---|---|---|
| 6' | 6.45 (1H, d, 8.0 Hz) | 120.1 | H-2', 5' | H-2', H-5', H-7' |
| 7' | 2.87 (2H, ddd, 14.0, 8.0, 4.0 Hz) | 36.1 | H-8' | H-2', H-5', H-6', H-8' |
| 8' | 4.92 (1H, dd, 8.0, 4.0 Hz) | 72.9 | H-7' | H-7' |
| 9' | — | 170.6 | | H-7', H-8' |
| 1" | — | 126.0 | | H-5" |
| 2" | 6.43 (1H, d, 2.0 Hz) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 9.0 Hz) | 115.3 | H-6" | |
| 6" | 6.43 (1H, dd, 8.5, 2.0 Hz) | 122.9 | H-2", 5" | H-2", H-7" |
| 7" | 7.69 (1H, s) | 141.1 | | H-2", H-6" |
| 8" | — | 123.3 | | |
| 9" | — | 168.4 | | H-7" |

Trial Example

1. Materials

Animals: all animal procedures were approved by Animal Ethics Committee of China Pharmaceutical University. Male Sprague-Dawley rats (body weight: 250-300 g) were purchased from the Aier Maite Technology Corporation (Suzhou, China). The rats were housed in humidity- and temperature-controlled environment with a 12 h light:12 h dark cycle. Water and standard laboratory diet were available ad libitum.

Drugs and Reagents

Samples were prepared by the method of Example 1.

2. Protocol

Rats were randomly assigned into three groups: the treatment group (CP), the myocardial infarction group (MI) and the sham group.

MI was produced by following procedure: rats were anesthetized with chloral hydrate (300 mg/kg i.p.) and ventilated by a respirator (HX-100E, Taimeng Co. Ltd., China) with a tidal volume of 10 ml/kg and a respiratory rate of 80 cycles per minute. A left thoracotomy was performed in the fourth intercostal space, and then MI was induced by ligation of the LAD artery 2 mm from the tip of the left auricle. The sham-operated rats underwent the same thoracotomy without LAD ligation. Electrocardiogram was recorded before and after operation procedures. MI was confirmed by ST segment elevation in the electrocardiogram and the appearance of epicardial cyanosis.

The samples (corresponding concentrations of 20 mg/kg, prepared by the method of Example 1) in the treatment group (CP) were given once daily by oral administration for 3 days before MI. The sham and MI group received only saline.

At the end of 6 h ischemic period, a catheter was inserted into the left ventricle for evaluating cardiac function. Left ventricular end diastolic pressure (LVEDP), left ventricular systolic pressure (LVSP), +dP/dt and −dP/dt were recorded through a biological mechanic experiment system (BL420, Taimeng Co. Ltd., China). Cardiac marker enzymes including creatine kinase-MB (CK-MB) and lactate dehydrogenase (LDH) were tested for estimation of myocardial cell damage using commercial kits (Jiancheng Bioengineering Institute, China). Tumor necrosis factor-α (TNF-α) level in serum was measured using a commercial ELISA kit (R&D, USA). At the end of experiment, the heart was excised, sliced into five sections, and infarct size was measured using 2,3,5-triphenyltetrazolium chloride (TTC) staining to assess myocardial injury as reported previously. Sections were photographed and the area at risk was quantified with the aid of the Image-Pro Plus 6 software.

Figure 11A:
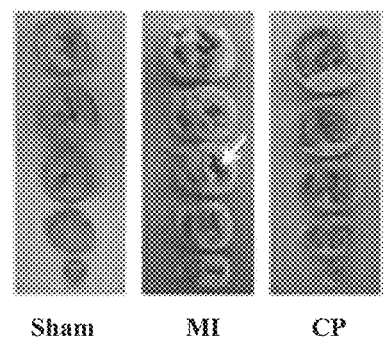
FIG. 11A was the TIC-stained heart.
Figure 11B:
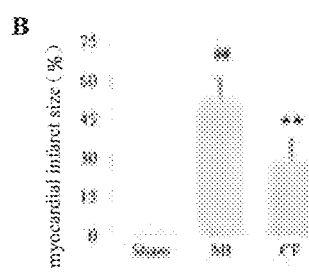
FIG. 11B~11G were the schematic diagrams of the myocardial infarct size, serum level of CK-MB, serum level of LDH, level of TNF-α, cardiac diastole and cardiac systole.

3. Results 3.1 FIG. 11A showed the TIC-stained heart. Compared with the MI group, pre-treatment by the traditional Chinese medicine composition of the present invention could markablely reduce the infarct size (FIG. 1B, treatment group 29.4±4.0% vs MI group 53.3±3.7%, p=0.0016, n=5, one-way ANOVA, Dunnett test).

Figure 11C:
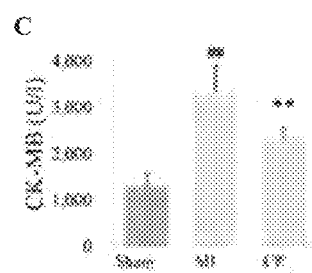
Figure 11D:
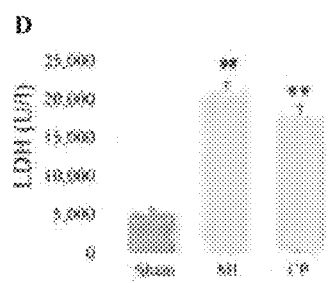

3.2 MI resulted in marked elevation in the serum levels of CK and LDH (FIG. 11C, FIG. 11D). The composition of the present invention could inhibit MI-caused increases in the activities of the enzymes (FIG. 11C and FIG. 11D, treatment group vs MI group, P<0.0001, CK experiment, P<0.0001 LDH experiment, n=8, one-way ANOVA, Dunnett test).

Figure 11E:
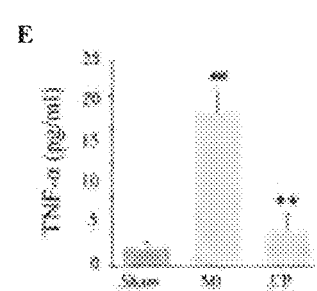
Figure 11F:
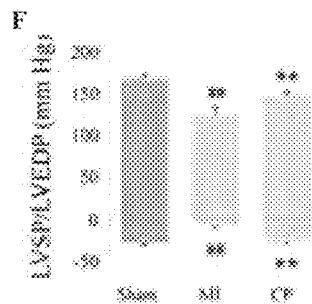
Figure 11G:
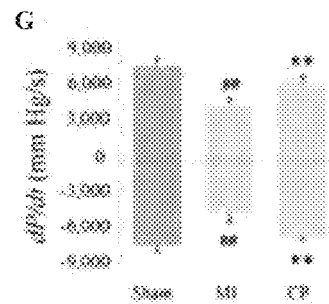

3.3 MI could cause markedly increased TNF-α. Pre-treatment by the composition of the present invention could alleviate the increased TNF-α (FIG. 11E, treatment group vs MI group, P<0.0001, n=8, one-way ANOVA, Dunnett test). Compared with the sham group, LVEDP was increased while LVSP, maximal rate of increase of LV pressure (+dP/dt) and maximal rate of decrease of LV pressure (−dP/dt) were decreased post-MI (FIG. 11F and FIG. 11G). The traditional Chinese medicine composition of the present invention showed a significantly improving effect on the heart's diastolic and systolic functions (FIG. 11F and FIG. 11G).

What claimed is:

1. A Chinese medicine composition comprising the following materials by weight percentage: 30%~80% of phenolic acid derivatives, 2%~10% of tanshinones and 15%~60% of saponines,
    wherein said phenolic acid derivatives consist of the following ingredients by weight parts: Danshensu:protocatechuic acid:protocatechuic aldehyde:caffeic acid:Salvianolic acid U+Salvianolic acid T:rosmarinic acid:lithospermic acid:Salvianolic acid B:Salvianolic acid A:Salvianolic acid G isomer:Salvianolic acid G:Salvianolic D=(2~6):(0.01~0.05):(1~3):(0.01~0.06):(0.5~2):(0.2~1):(0.05~0.3):(0.5~2):(0.2~1):(0.1~0.5):(0.1~0.5):(0.2~1),
    wherein said tanshinones consist of the following ingredients by weight parts: Dihydrotanshinone I:tanshinone I:cryptotanshinone:tanshinone IIA:Danshenxinkun D=(0.01~0.05):(0.05~0.1):(0.02~0.1):(0.1~0.5):(0.1~0.5), and
    wherein said saponines consist of the following ingredients by weight parts: Panax Notoginseng Saponin R1:Ginsenoside Rg1 and/or Re and/or Rh2:Ginsenoside Rb1:Ginsenoside Rh1-S:Ginsenoside Rd and/or Rh1-R=(0.1~0.5):(1~4):(1~4):(0.2~0.7):(0.2~0.7).

2. The composition according to claim 1, wherein said composition comprises the following materials by weight percentage: 50%~70% of phenolic acid derivatives, 2%~6% of tanshinones and 25%~45% of saponines.

3. The composition according to claim 1, wherein said composition consist of the following materials by weight percentage: 66% of phenolic acid derivatives, 3% of tanshinones and 31% of saponines.

4. The composition according to claim 1, wherein said phenolic acid derivatives consist of the following ingredients by weight parts: Danshensu:protocatechuic acid:protocatechuic aldehyde:caffeic acid:Salvianolic acid U+Salvianolic acid T:rosmarinic acid:lithospermic acid:Salvianolic acid B:Salvianolic acid A:Salvianolic acid G isomer:Salvianolic acid G:Salvianolic D=(3.31~4.82):(0.02~0.03):(1.17~1.54):(0.03~0.04):(0.86~1.13):(0.48~0.63):(0.12~0.16):(1~2):(0.44~0.58):(0.27~0.36):(0.29~0.38):(0.54~0.64).

5. The composition according to claim 1, wherein said phenolic acid derivatives consist of the following ingredients by weight parts: Danshensu:protocatechuic acid:Salvianolic acid U+Salvianolic acid T:Salvianolic D:Salvianolic acid G:rosmarinic acid:lithospermic acid:Salvianolic acid B:Salvianolic acid A=(3~5):(1~2):(0.5~2):(0.3~0.8):(0.1~0.5):(0.3~1.5):(0.1~0.3):(0.5~2):(0.5~1.5).

6. The composition according to claim 5, wherein said phenolic acid derivatives consist of the following ingredients by weight parts: Danshensu:protocatechuic acid:Salvianolic acid U+Salvianolic acid T:Salvianolic D:Salvianolic acid G:rosmarinic acid:lithospermic acid:Salvianolic acid B:Salvianolic acid A=3.52:1.38:1.1:0.58:0.33:0.79:0.17:1.32:0.93.

7. The composition according to claim 1, wherein said tanshinones consist of the following ingredients by weight parts: Dihydrotanshinone I:tanshinone I:cryptotanshinone:tanshinone IIA:Danshenxinkun D=(0.02~0.03):(0.06~0.07):(0.04~0.06):(0.21~0.27):(0.22~0.28).

8. The composition according to 1, wherein said tanshinones consist of the following ingredients by weight parts: Dihydrotanshinone I:tanshinone I:cryptotanshinone:tanshinone IIA=(0.01~0.05):(0.05~0.1):(0.02~0.1):(0.1~0.5).

9. The composition according to claim 8, wherein said tanshinones consist of the following ingredients by weight parts: Dihydrotanshinone I:tanshinone I:cryptotanshinone:tanshinone IIA=0.03:0.08:0.03:0.26.

10. The composition according to claim 1, wherein said saponines consist of the following ingredients by weight parts: *Panax Notoginseng* Saponin R1:Ginsenoside Rg1 and/or Re and/or Rh2:Ginsenoside Rb1:Ginsenoside Rh1-S:Ginsenoside Rd and/or Rh1-R=(0.2~0.3):(1.9~3.0):(1.9~3.0):(0.48~0.51):(0.47~0.62).

11. The composition according to claim 10, wherein said Ginsenoside Rg1 and Ginsenoside Re coexist in a ratio of (16~17):1 by weight parts.

12. A preparation comprising the Chinese medicine composition according to claim 1 and a pharmaceutically acceptable carrier, the weight percentage of said composition in the preparation is 0.1%~99.9% and the balance is the pharmaceutically acceptable carrier.

13. The preparation according to claim 12, wherein said pharmaceutical preparation is in a dosage form of a tablet, drop pill or micro drop pill.

14. The preparation according to claim 13, wherein said pharmaceutical preparation is in a dosage form of a tablet.

15. The preparation according to claim 13, wherein said pharmaceutical preparation is in a dosage form of a drop pill.

16. The preparation according to claim 13, wherein said pharmaceutical preparation is in a dosage form of a micro drop pill.

17. A preparation comprising the Chinese medicine composition according to claim 2 and a pharmaceutically acceptable carrier, the weight percentage of said composition in the preparation is 0.1%~99.9% and the balance is the pharmaceutically acceptable carrier, said pharmaceutical preparation is in a dosage form of a tablet, drop pill or micro drop pill.

18. The preparation according to claim 17, wherein said pharmaceutical preparation is in a dosage form of a tablet.

19. The preparation according to claim 17, wherein said pharmaceutical preparation is in a dosage form of a drop pill.

20. The preparation according to claim 17, wherein said pharmaceutical preparation is in a dosage form of a micro drop pill.

* * * * *